(12) United States Patent
Hirosaki et al.

(10) Patent No.: US 8,389,197 B2
(45) Date of Patent: *Mar. 5, 2013

(54) COMPOUND, POSITIVE RESIST COMPOSITION AND RESIST PATTERN FORMING METHOD

(75) Inventors: Takako Hirosaki, Kawasaki (JP); Daiju Shiono, Kawasaki (JP); Taku Hirayama, Kawasaki (JP); Hideo Hada, Kawasaki (JP)

(73) Assignee: Tokyo Ohka Kogyo Co., Ltd., Kawasaki-shi (JP)

( * ) Notice: Subject to any disclaimer, the term of this patent is extended or adjusted under 35 U.S.C. 154(b) by 858 days.

This patent is subject to a terminal disclaimer.

(21) Appl. No.: 11/994,602

(22) PCT Filed: Jun. 30, 2006

(86) PCT No.: PCT/JP2006/313103
§ 371 (c)(1),
(2), (4) Date: Jan. 3, 2008

(87) PCT Pub. No.: WO2007/004566
PCT Pub. Date: Jan. 11, 2007

(65) Prior Publication Data
US 2009/0117488 A1  May 7, 2009

(30) Foreign Application Priority Data
Jul. 5, 2005 (JP) .................. 2005-196132

(51) Int. Cl.
G03F 7/004 (2006.01)
G03F 7/039 (2006.01)
G03F 7/20 (2006.01)
G03F 7/30 (2006.01)

(52) U.S. Cl. ............... 430/270.1; 430/311; 430/326; 430/905; 430/908; 430/914; 568/720; 568/723; 568/729; 568/744

(58) Field of Classification Search .................. None
See application file for complete search history.

(56) References Cited

U.S. PATENT DOCUMENTS

| | | | |
|---|---|---|---|
| 4,465,765 A | 8/1984 | Leppard et al. | |
| 5,286,600 A | 2/1994 | Ochiai et al. | |
| 5,389,491 A | 2/1995 | Tani et al. | |
| 5,658,706 A * | 8/1997 | Niki et al. | 430/270.1 |
| 5,693,452 A | 12/1997 | Aoai et al. | |
| 5,707,776 A | 1/1998 | Kawabe et al. | |
| 5,824,451 A | 10/1998 | Aoai et al. | |
| 5,837,420 A | 11/1998 | Aoai et al. | |

(Continued)

FOREIGN PATENT DOCUMENTS

| | | |
|---|---|---|
| CN | 1611490 | 5/2005 |
| JP | A-59-053846 | 3/1984 |

(Continued)

OTHER PUBLICATIONS

Hirayama et al ("Development of Electron Beam Resists Based on Amorphous Polyphenols with Low Molecular Weight and Narrow Dispersion", Proceedings of SPIE vol. 5753, p. 738-745).*

(Continued)

Primary Examiner — Sin J. Lee
(74) Attorney, Agent, or Firm — Knobbe Martens Olson & Bear LLP

(57) ABSTRACT

The present invention provides a positive resist composition and a resist pattern forming method that are capable of forming a resist pattern with a reduced level of roughness. The positive resist composition includes the compound represented by the general formula (I) below. The present invention also provides the resist pattern forming method using the positive resist composition above.

[Chemical formula 1]

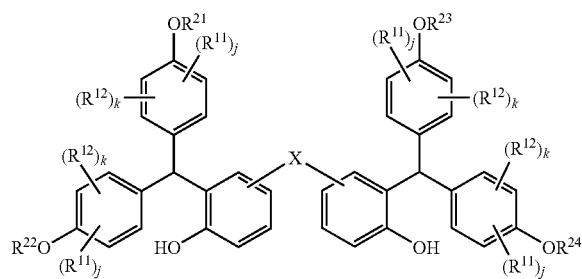

(I)

[wherein, in formula (I), $R^{11}$ and $R^{12}$ each represents, independently, an alkyl group of 1 to 10 carbon atoms or an aromatic hydrocarbon group, and may include a hetero atom in the structure thereof; $R^{21}$ to $R^{24}$ each represents, independently, a hydrogen atom or an acid dissociable, dissolution inhibiting group, and two of the $R^{21}$ to $R^{24}$ represents a hydrogen atom and the others represents an acid dissociable, dissolution inhibiting group; X is a group represented by general formulas (Ia) or (Ib) below].

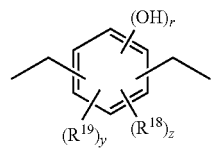

(Ia)

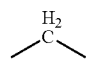

(Ib)

8 Claims, No Drawings

U.S. PATENT DOCUMENTS

| | | | |
|---|---|---|---|
| 5,844,057 | A | 12/1998 | Watanabe et al. |
| 5,994,025 | A | 11/1999 | Iwasa et al. |
| 6,037,098 | A | 3/2000 | Aoai et al. |
| 6,106,993 | A | 8/2000 | Watanabe et al. |
| 6,165,677 | A | 12/2000 | Yako |
| 6,197,473 | B1 | 3/2001 | Kihara et al. |
| 6,638,683 | B1 | 10/2003 | Tan et al. |
| 7,220,808 | B2 | 5/2007 | Yamagishi et al. |
| 7,504,196 | B2 | 3/2009 | Shiono et al. |
| 2002/0025495 | A1 | 2/2002 | Ogata et al. |
| 2002/0058205 | A1 | 5/2002 | Nakashima et al. |
| 2003/0232277 | A1 | 12/2003 | Sasaki et al. |
| 2004/0005512 | A1 | 1/2004 | Mizutani et al. |
| 2004/0234885 | A1 | 11/2004 | Watanabe et al. |
| 2005/0058935 | A1 | 3/2005 | Kishimura et al. |
| 2005/0130057 | A1 | 6/2005 | Sudo et al. |
| 2005/0271971 | A1 | 12/2005 | Ueda et al. |
| 2007/0059632 | A1 | 3/2007 | Oguro et al. |
| 2007/0259273 | A1 | 11/2007 | Shiono et al. |
| 2007/0281243 | A1 | 12/2007 | Hirayama |
| 2008/0020288 | A1 | 1/2008 | Hirayama et al. |
| 2008/0145784 | A1 | 6/2008 | Shiono et al. |
| 2009/0117488 | A1 | 5/2009 | Hirosaki et al. |
| 2009/0162781 | A1* | 6/2009 | Shiono et al. ............ 430/270.1 |

FOREIGN PATENT DOCUMENTS

| | | |
|---|---|---|
| JP | H05-061197 | 3/1993 |
| JP | H05-249681 | 9/1993 |
| JP | A-06-083055 | 3/1994 |
| JP | H06-059444 | 3/1994 |
| JP | H06-167811 | 6/1994 |
| JP | H06-266109 | 9/1994 |
| JP | A-08-123031 | 5/1996 |
| JP | 08-193054 | 7/1996 |
| JP | H08-220740 | 8/1996 |
| JP | 08-262712 | 10/1996 |
| JP | H08-262712 | 10/1996 |
| JP | H08-337616 | 12/1996 |
| JP | H09-005999 | 1/1997 |
| JP | H09-160246 | 6/1997 |
| JP | A-09-211865 | 8/1997 |
| JP | H09-211866 | 8/1997 |
| JP | H10-123703 | 5/1998 |
| JP | H10-274845 | 10/1998 |
| JP | A-11-153863 | 6/1999 |
| JP | H11-167199 | 6/1999 |
| JP | 11-199533 | 7/1999 |
| JP | 2000-086584 | 3/2000 |
| JP | 2000-305270 | 11/2000 |
| JP | 2000-330282 | 11/2000 |
| JP | 2001-312055 | 11/2001 |
| JP | 2002-99088 | 4/2002 |
| JP | 2002-99089 | 4/2002 |
| JP | 2002-221787 | 8/2002 |
| JP | A-2002-328473 | 11/2002 |
| JP | 2003-30282 | 1/2003 |
| JP | A-2003-084437 | 3/2003 |
| JP | 2003-183227 | 7/2003 |
| JP | 2003-260881 | 9/2003 |
| JP | 2004-062049 | 2/2004 |
| JP | 2004-125835 | 4/2004 |
| JP | 2004-151605 | 5/2004 |
| JP | A-2004-191913 | 7/2004 |
| JP | 2004-302440 | 10/2004 |
| JP | 2004-359590 | 12/2004 |
| JP | 2002-055452 | 2/2005 |
| JP | 2005-089387 | 4/2005 |
| JP | 2005-091909 | 4/2005 |
| JP | 2005-309421 | 11/2005 |
| JP | A-2007-015944 | 1/2007 |
| KR | 10-231242 | 5/1997 |
| KR | 2001-0088341 | 9/2001 |
| KR | 10-0406242 | 11/2003 |
| TW | 200302397 A | 8/2003 |
| TW | 200617602 | 6/2006 |
| WO | WO 03/069412 A1 | 8/2003 |
| WO | WO 2005/029189 A1 | 3/2005 |
| WO | WO2006/046383 * | 5/2006 |

OTHER PUBLICATIONS

International Search Report in connection with corresponding PCT application No. PCT/JP2006/313103, dated Sep. 26, 2006.

Hirayama et al., *Journal of Photopolymer* Science and Technology, vol. 17, No. 3, 435-440, (2004).

Hirayama, T., et al. "Depth Profile and Line-Edge Roughness of Low-Molecular-Weight Amorphous Electron Beam Resists", The Japan Journal of Applied Physics, vol. 44, No. 7B, 2005, pp. 5484-5488 (published on Jul. 26, 2005).

International Search Report issued in corresponding PCT application No. PCT/JP2006/302271, mailed on Mar. 7, 2006.

International Search Report issued in corresponding PCT application No. PCT/JP2006/311443, dated Jun. 7, 2006.

International Search Report issued in corresponding PCT application No. PCT/JP2006/301679, dated Feb. 16, 2006.

Office Action issued in counterpart Japanese Patent Application No. 2005-026266, dated Mar. 3, 2009.

Office Action issued in counterpart Korean Patent Application No. 10-2007-7017441, dated May 7, 2009.

Office Action issued in the counterpart Japanese Patent Application No. 2005-050721, dated Mar. 3, 2009.

Office Action issued in Apr. 14, 2008 on the counterpart Korean Patent Application No. 10-2007-7004390.

Office Action issued in Aug. 26, 2008, on the counterpart Japanese Patent Application No. 2004-182301.

Office Action issued in corresponding Japanese Patent Application No. 2004-260764, dated Mar. 3, 2009.

Office Action issued in counterpart Japanese Patent Application No. JP 2005-050721, dated Jul. 28, 2009.

Office Action issued in Jun. 3, 2008, on the counterpart Japanese Application No. 2004-182301.

Office Action issued in Jun. 5, 2008 on the counterpart Korean Patent Application No. 10-2007-7019433.

Office Action issued in Korean Patent Application No. 10-2007-7004390, dated Dec. 17, 2008.

Office Action issued in Korean Patent Application No. 10-2008-7025851, dated Jan. 7, 2009.

Office Action issued in May 12, 2008, in the counterpart Taiwanese Patent Application No. 094104523.

Office Action issued in May 27, 2008, on the counterpart Japanese Application No. 2004-182300.

Yamaguchi et al., Linewidth fluctuations caused by polymer aggregates in resist films, Journal of Photopolymer Science and Technology, vol. 10, No. 4, pp. 635-640, (1997).

International Search Report issued in corresponding PCT application No. PCT/JP2005/013564, mailed Sep. 6, 2005.

International Search Report issued in corresponding PCT application No. PCT/JP2005/018143, mailed Nov. 15, 2005.

Office Action issued Sep. 16, 2008 in the counterpart Korean Patent Application No. 10-20077010473.

Notice of Allowance issued in related Korean Patent Application No. 10-2009-7006750, dated Feb. 16, 2010.

Decision to Grant a Patent issued in corresponding Japanese Patent Application No. JP 2004-182301, dated Jan. 6, 2009.

Hirayama et al, "Development of Amorphous PolyPhenol Resists with Low Molecular Weight and Narrow Dispersion for EB Lithography", IEEE Xplore, Oct. 22, 2004, pp. 10-11.

Notice of Allowance issued on corresponding Japanese Patent Application No. 2004-260764, dated Feb. 16, 2010.

Office Action issued in corresponding U.S. Appl. No. 10/590,046, dated Mar. 17, 2010.

Office Action issued in corresponding U.S. Appl. No. 10/590,046, dated Sep. 21, 2009.

Office Action issued in corresponding U.S. Appl. No. 10/590,046, dated Apr. 24, 2009.

Office Action issued in corresponding U.S. Appl. No. 10/590,046, dated Sep. 26, 2008.

Office Action issued in corresponding U.S. Appl. No. 11/572,630, dated Mar. 1, 2010.
Office Action issued in corresponding U.S. Appl. No. 11/572,630, dated Aug. 13, 2009.
Office Action issued in corresponding U.S. Appl. No. 11/572,630, dated Apr. 23, 2009.
Office Action issued in corresponding U.S. Appl. No. 11/572,630, dated Sep. 25, 2008.
Office Action issued in corresponding U.S. Appl. No. 11/574,805 dated Feb. 26, 2010.
Office Action issued in corresponding U.S. Appl. No. 11/574,805 dated Aug. 4, 2009.
Office Action issued in corresponding U.S. Appl. No. 11/574,805 dated May 19, 2009.
Office Action issued in corresponding U.S. Appl. No. 11/574,805 dated Aug. 19, 2008.
Office Action issued in corresponding U.S. Appl. No. 11/574,805 dated Feb. 10, 2009.
Office Action issued in corresponding U.S. Appl. No. 11/718,091 dated Apr. 23, 2010.
Office Action issued in corresponding U.S. Appl. No. 11/718,091 dated Sep. 14, 2009.
Office Action issued in corresponding U.S. Appl. No. 11/813,511, dated Apr. 28, 2010.
Office Action issued in corresponding U.S. Appl. No. 11/813,511, dated Oct. 8, 2009.
Office Action issued in corresponding U.S. Appl. No. 11/884,748, dated Jul. 7, 2008.
Office Action issued in corresponding U.S. Appl. No. 11/914,451 dated May 3, 2010.
Office Action issued in corresponding U.S. Appl. No. 11/914,451 dated Oct. 8, 2009.
Office Action issued in corresponding U.S. Appl. No. 11/917,458, dated Apr. 5, 2010.
Office Action in corresponding European Patent Application No. 06732357.6 dated Aug. 15, 2011.
Office Action in corresponding Chinese Patent Application No. 200680016732.3 dated Aug. 24, 2011.
Notice of Allowance in corresponding Japanese Patent Application No. 2005-212904 dated Sep. 20, 2011.
European Search Report issued on counterpart European Patent Application No. EP 10194369.4, dated Feb. 17, 2011.
Office Action issued in related U.S. Appl. No. 11/572,630, dated Jul. 12, 2010.
Office Action issued in related U.S. Appl. No. 10/590,046, dated Jul. 20, 2010.
Office Action issued in related U.S. Appl. No. 11/574,805 dated Jul. 1, 2010.
European Search Report issued on counterpart European Patent Application No. EP 05788289.6, dated Jul. 26, 2010.
Notice of Allowance issued in related U.S. Appl. No. 11/718,091 dated Aug. 10, 2010.
Notice of Allowance issued in related U.S. Appl. No. 11/917,458, dated Sep. 7, 2010.

* cited by examiner

COMPOUND, POSITIVE RESIST COMPOSITION AND RESIST PATTERN FORMING METHOD

TECHNICAL FIELD OF THE INVENTION

The present invention relates to a compound that is ideal for use within the positive resist composition, a positive resist composition and a resist pattern forming method.

Priority is claimed on Japanese Patent Application No. 2005-196132, filed Jul. 5, 2005, the content of which is incorporated herein by reference.

BACKGROUND OF THE INVENTION

In recent years, in the production of semiconductor elements and liquid crystal display elements, advances in lithography techniques have lead to rapid progress in the field of pattern miniaturization.

Typically, these miniaturization techniques involve shortening the wavelength of the exposure light source. Conventionally, ultra violet radiation typified by g-line and i-line radiation has been used, but nowadays, mass production of semiconductor elements using KrF excimer lasers and ArF excimer lasers has commenced. Furthermore, investigation is also being conducted into radiation with even shorter wavelengths than these excimer lasers, including $F_2$ excimer lasers, electron beams, EUV (extreme ultra violet), and X-rays.

Furthermore, one example of a known pattern-forming material capable of forming a pattern of minute dimensions is a chemically amplified resist, which includes a base material component with a film-forming capability, and an acid generator component that generates an acid upon exposure. Chemically amplified resists include negative resists, which undergo a reduction in alkali solubility on exposure, and positive resists, which exhibit increased alkali solubility on exposure.

Conventionally, polymers have been used as the base material components within these types of chemically amplified resists, and examples of these polymers include polyhydroxystyrene (PHS), PHS-based resins in which a portion of the hydroxyl groups of PHS have been protected with acid-dissociable, dissolution-inhibiting groups, copolymers derived from (meth)acrylate esters, and resins in which a portion of the carboxyl groups within these (meth)acrylate esters have been protected with acid-dissociable, dissolution-inhibiting groups.

However, when a pattern is formed using these types of pattern-forming materials, a problem arises in that roughness can develop on the upper surface and side wall surfaces of the pattern. For example, roughness on the side wall surfaces of a resist pattern, so-called line edge roughness (LER), can cause distortions around the holes in hole patterns, and fluctuations in the line width in line and space patterns, and consequently has the potential to adversely affect the formation of very fine semiconductor elements.

This problem becomes more significant as the pattern dimensions are reduced. Accordingly, in lithography processes using electron beams or EUV or the like, which are targeting the formation of very fine patterns with dimensions of several dozen nm, very low levels of roughness that are superior to current levels of pattern roughness are being demanded.

However, the polymers typically used as base materials have a large molecular size (or root mean squared radius per molecule) of several nm. In the developing step of a pattern formation process, the solubility behavior of the resist with respect to the developing solution typically occurs in single molecule units of the base material component, meaning that as long as polymers are used as the base material component, further reductions in the level of roughness will remain extremely difficult to achieve.

In order to overcome this type of problem, resists that employ a low molecular weight material as the base material component have been proposed as potential materials for achieving lower levels of roughness. For example, patent references 1 and 2 propose low molecular weight materials that include alkali-soluble groups such as hydroxyl groups, wherein either a portion of, or all of, these groups have been protected with acid-dissociable, dissolution-inhibiting groups. These low molecular weight materials have small molecular sizes as a result of their lower molecular weight, and as such, are expected to enable reductions in the level of roughness.

[Patent Reference 1]
Japanese Unexamined Patent Application, First Publication No. 2002-099088

[Patent Reference 2]
Japanese Unexamined Patent Application, First Publication No. 2002-099089

DISCLOSURE OF THE INVENTION

Problems to be Solved by the Invention

However, using these materials, the formation of high resolution patterns with reduced roughness, such as very fine patterns with dimensions of less than 90 nm, at a level that enables their practical application has proven very difficult. Problems include an inability to form a pattern at all (an inferior pattern-forming capability), or even if a pattern is able to be formed, an unsatisfactory reduction in the level of roughness, or an inability to satisfactorily maintain the pattern shape (a low pattern retention capability).

The present invention takes the above circumstances into consideration, with an object of providing a positive resist composition that are capable of forming a resist pattern with a reduced level of roughness, a resist pattern forming method and a compound that is ideal for use within the positive resist composition.

Means for Solving the Problem

The present inventors have focused on and extensively studied the protection state of phenolic hydroxyl groups of a base material component at the molecular level, and found that the above object can be achieved by a compound in which a specific position of the phenolic hydroxyl group of a specific polyphenol compound was protected with a specific number of an acid dissociable, dissolution inhibiting group, and thus the present invention was achieved.

In other words, a first aspect of the present invention is a compound represented by the general formula (I) below.

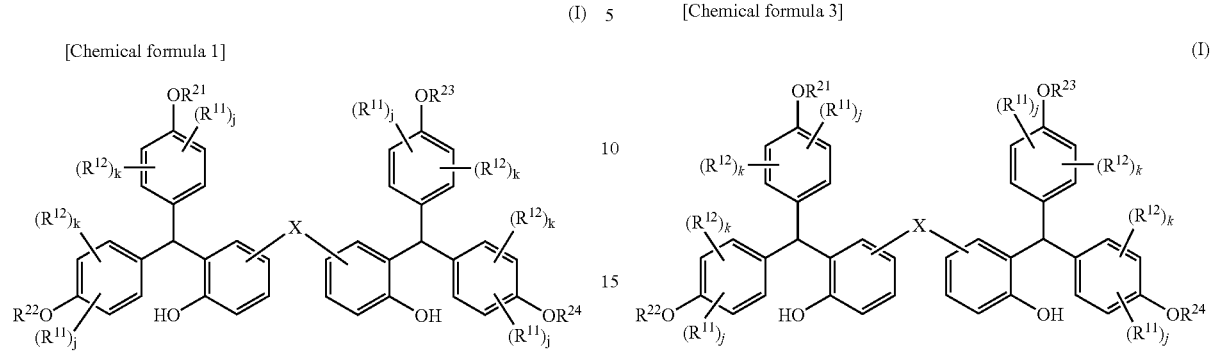

[wherein, in formula (I), $R^{11}$ and $R^{12}$ each represents, independently, an alkyl group of 1 to 10 carbon atoms or an aromatic hydrocarbon group, and may include a hetero atom in the structure thereof, $R^{21}$ to $R^{24}$ each represents, independently, a hydrogen atom or an acid dissociable, dissolution inhibiting group, and two of the group of $R^{21}$ to $R^{24}$ represent a hydrogen atom and the others represents an acid dissociable, dissolution inhibiting group; j and k each represents, independently, an integer of 0 or 1 or more, and j+k is 4 or less; X is a group represented by general formulas (Ia) or (Ib) below].

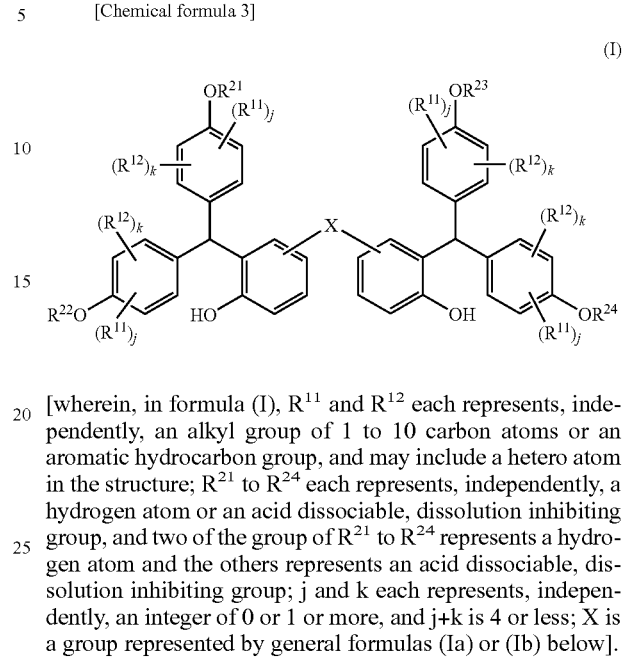

[wherein, in formula (Ia), $R^{18}$ and $R^{19}$ each represents, independently, an alkyl group of 1 to 10 carbon atoms or an aromatic hydrocarbon group, and may include a hetero atom in the structure; and r, y, and z each represents, independently, an integer of 0 or 1 or more, and r+y+z represents 4 or less].

A second aspect of the present invention is a positive resist composition including a base material component (A) which exhibits increased alkali solubility under an action of an acid, and an acid generator component (B) which generates an acid upon exposure, wherein the base material component (A) is a compound (A1) represented by a general formula (I) below.

[wherein, in formula (I), $R^{11}$ and $R^{12}$ each represents, independently, an alkyl group of 1 to 10 carbon atoms or an aromatic hydrocarbon group, and may include a hetero atom in the structure; $R^{21}$ to $R^{24}$ each represents, independently, a hydrogen atom or an acid dissociable, dissolution inhibiting group, and two of the group of $R^{21}$ to $R^{24}$ represents a hydrogen atom and the others represents an acid dissociable, dissolution inhibiting group; j and k each represents, independently, an integer of 0 or 1 or more, and j+k is 4 or less; X is a group represented by general formulas (Ia) or (Ib) below].

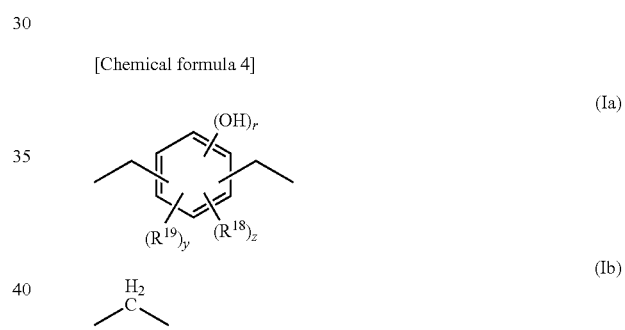

[wherein, in formula (Ia), $R^{18}$ and $R^{19}$ each represents, independently, an alkyl group of 1 to 10 carbon atoms or an aromatic hydrocarbon group, and may include a hetero atom in the structure; and r, y, and z each represents, independently, an integer of 0 or 1 or more, and r+y+z represents 4 or less].

A third aspect of the present invention is a resist pattern forming method that includes the steps of: forming a resist film on a substrate using a positive resist composition according to the second aspect described above, conducting exposure of the resist film, and developing the resist film to form the resist pattern.

In the claims and the specification of the present invention, unless stated otherwise, the term "alkyl group" refers to a straight-chained, branched-chained or cyclic monovalent saturated hydrocarbon group.

The term "exposure" is a general concept that includes irradiation with any form of radiation.

EFFECTS OF THE INVENTION

The present invention provides a positive resist composition and a resist pattern forming method that are capable of forming a resist pattern with a reduced level of roughness, and a compound that is ideal for use within the positive resist composition.

Embodiments of the Invention

<<Compound>>

A compound of the present invention (hereafter referred to as the compound (A1)) is a compound represented by the general formula (I) above.

When the compound (A1) is blended into a resist composition together with an acid generator component (B) that generates acid upon exposure, the action of the acid generated from the acid generator component (B) by exposure causes the acid-dissociable, dissolution-Inhibiting groups within the compound (A1) to dissociate, thereby causing the entire compound (A1) to shift from an alkali-insoluble state to an alkali-soluble state.

In general formula (I) shown above, j and k each represents, independently, an integer of 0 or 1 or more, and j+k is 4 or less, preferably an integer of 0 to 2, more preferably 0 or 1, most preferably 1.

$R^{11}$ and $R^{12}$ each represents, independently, a straight-chained, branched-chained or cyclic alkyl group of 1 to 10 carbon atoms, or an aromatic hydrocarbon group.

The alkyl group is preferably a straight-chained or branched-chained lower alkyl group of 1 to 5 carbon atoms, or a cyclic alkyl group of 5 to 6 carbon atoms.

Specific examples of the lower alkyl groups include a straight-chained or branched-chained alkyl group such as a methyl group, ethyl group, propyl group, isopropyl group, n-butyl group, isobutyl group, tert-butyl group, pentyl group, isopentyl group, and neopentyl group, of these, a methyl group is preferable.

Specific examples of the cyclic alkyl group include a cyclohexyl group and cyclopentyl group.

The aromatic hydrocarbon group preferably has 6 to 15 carbon atoms, and specific examples thereof include a phenyl group, a tolyl group, a xylyl group, a mesityl group, a phenethyl group, and a naphthyl group.

These alkyl group or aromatic hydrocarbon group may include a hetero atom such as an oxygen atom, a nitrogen atom, or a sulfur atom in the structure.

In the compound (A1), although there are no particular restrictions on the bonding position between $R^{11}$ and $R^{12}$, in view of the excellent effects of the present invention, it is preferable that $R^{11}$ or $R^{12}$ bonds to at least one carbon atom adjacent to a carbon atom which bonds —$OR^{21}$ to —$OR^{24}$ (an ortho-positioned carbon atom), preferably, according to a compound (A1-1) represented by a general formula (II) below, $R^{11}$ bonds to the other ortho-positioned carbon atom of a carbon atom which bonds —$OR^{21}$ to —$OR^{24}$, and $R^{12}$ bonds at para position of the $R^{11}$.

X is a group represented by the general formulas (Ia) and (Ib) above,

In the formula (Ia), $R^{18}$ and $R^{19}$ each represents, independently, an alkyl group of 1 to 10 carbon atoms or an aromatic hydrocarbon group, and may include a hetero atom in the structure in the same manner as $R^{11}$ and $R^{12}$.

The aromatic hydrocarbon group preferably has 6 to 15 carbon atoms, and specific examples thereof include a phenyl group, a tolyl group, a xylyl group, a mesityl group, a phenethyl group, and a naphthyl group.

r, y, and z each represents, independently, an integer of 0 or 1 or more, and r+y+z represents 4 or less.

X is most preferably a group represented by general formula (Ib) shown above because it is easily synthesized.

$R^{21}$ to $R^{24}$ each represents, independently, a hydrogen atom or an acid dissociable, dissolution inhibiting group and two of the $R^{21}$ to $R^{24}$ represent a hydrogen atom and the others represent an acid dissociable, dissolution inhibiting group.

The acid dissociable, dissolution inhibiting groups are groups which have alkali dissolution inhibition properties that cause the entire component (A1) to change to an alkali-insoluble state before dissociation, and which cause the entire compound (A1) to change to an alkali-soluble state after dissociation. Therefore, in the case where the compound (A1) is mixed with the positive resist composition, together with the component (B), an acid generated from the acid generator component (B) causes the acid-dissociable, dissolution-inhibiting groups to dissociate, causing the entire component (A) to change to an alkali-soluble state from an alkali-insoluble state.

There are no particular restrictions on the acid dissociable, dissolution inhibiting groups, provided they are acid dissociable, dissolution inhibiting groups selected appropriately from those proposed in a hydroxystyrene-based resin and a (meth)acrylate-based resin used in a chemically amplified photoresist composition for KrF or ArF.

Specific examples include a tertiary alkyl group, a tertiary alkyloxycarbonyl group, an alkoxycarbonylalkyl group, an alkoxyalkyl group, and a cyclic ether group.

Specific examples of the tertiary alkyl group are tertiary alkyl groups including chain tertiary alkyl groups such as a tert-butyl group and a tert-amyl group; and aliphatic polycyclic groups such as a 2-methyl-2-adamantyl group and a 2-ethyl-2-adamantyl group.

In the specification and claims, the term "aliphatic" is a relative concept used in relation to the term "aromatic", and defines a group or compound or the like that contains no aromaticity. The term "aliphatic cyclic group" describes a monocyclic group or polycyclic group that contains no aromaticity, and may be either saturated or unsaturated, but is preferably saturated.

The tertiary alkyl group in the tertiary alkyloxycarbonyl group includes the same groups as those described above, and specific examples include a tert-butyloxycarbonyl group and a tert-amyloxycarbonyl group.

Specific examples of the cyclic ether group include a tetrahydropyranyl group and a tetrahydrofuranyl group.

The present invention preferably includes at least one an acid dissociable, dissolution inhibiting group selected from the group consisting of an alkoxycarbonylalkyl group represented by the general formula (p1) below and an alkoxyalkyl group represented by the general formula (p2) below in view of the effects of the present invention.

[Chemical formula 5]

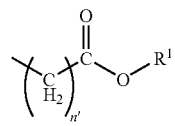
(p1)

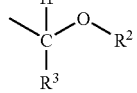
(p2)

[wherein, $R^1$ and $R^2$ each represents, independently, a straight-chained, branched-chained, or cyclic alkyl group, and may include a hetero atom in the structure thereof; $R^3$ represents a hydrogen atom or a lower alkyl group; and n' represents an integer from 1 to 3]

In general formula (p 1), n' represents an integer from 1 to 3, and preferably 1.

$R^1$ represents a straight-chained, branched-chained, or cyclic alkyl group, and may include a hetero atom in the structure. Namely, the alkyl group as $R^1$ is an alkyl group in which either a portion of, or all of, the hydrogen atoms may be substituted with a group containing a hetero atom (including the case of a hetero atom itself) and a portion of the carbon atoms may be substituted with hetero atoms.

Examples of the hetero atom include an oxygen atom, a sulfur atom, a nitrogen atom, and a fluorine atom.

The group containing a hetero atom may be a hetero atom itself, or a group composed of a hetero atom, a carbon atom and/or a hydrogen atom, for example, an alkoxy group.

Examples of the alkyl group in which either a portion of, or all of, hydrogen atoms are substituted with a group containing a hetero atom, include a fluorinated lower alkyl group of 1 to 5 carbon atoms in which either a portion of, or all of, the hydrogen atoms are substituted with a fluorine atom, a group in which two hydrogen atoms bonded to the same carbon atom are substituted with one oxygen atom (i.e., a group containing a carbonyl group (C=O)), and a group in which two hydrogen atoms bonded to the same carbon atom are substituted with one sulfur atom (i.e., a group containing a thiocarbonyl (C=S)).

Examples of the group in which a portion of the carbon atoms of the alkyl group are substituted with a group containing a hetero atom include a group in which carbon atoms are substituted with nitrogen atoms (for example, a group in which —CH$_2$— is substituted with —NH— in a branched-chained or cyclic alkyl group containing —CH$_2$— in the structure) and a group in which carbon atoms are substituted with oxygen atoms (for example, a group in which —CH$_2$— is substituted with —O— in a branched-chained or cyclic alkyl group containing —CH$_2$— in the structure).

The straight-chained alkyl group as $R_1$ preferably has 1 to 5 carbon atoms, and specific examples include a methyl group, an ethyl group, an n-propyl group, an n-butyl group, an isobutyl group, and an n-pentyl group, of which a methyl group or an ethyl group is preferred.

The branched-chained alkyl group as $R_1$ preferably has 4 to 10 carbon atoms and more preferably 4 to 8 carbon atoms, and specific examples include an isobutyl group, a tert-butyl group, an isopentyl group, a neopentyl group, and a tert-pentyl group, of which a tert-butyl group is preferred.

The cyclic alkyl group as $R_1$ preferably has 3 to 20 carbon atoms, preferably 4 to 14 carbon atoms, and most preferably 5 to 12 carbon atoms.

The structure of a basic ring (basic ring substituent group in which substituent groups have been removed) in the cyclic alkyl group may be either a monocyclic structure or a polycyclic structure, and a polycyclic structure is particularly preferred, in terms of achieving excellent effects for the present invention. The basic ring may be a hydrocarbon ring composed of carbons and hydrogens, or a heterocycle in which a portion of the carbon atoms that form the hydrocarbon ring are substituted with hetero atoms. In the present invention, the basic ring is particularly preferably a hydrocarbon ring. Examples of the hydrocarbon ring include monocycloalkanes, bicycloalkanes, tricycloalkanes, and tetracycloalkanes. Specific examples include monocycloalkanes such as cyclopentane and cyclohexane; and polycycloalkanes such as adamantane, norbornane, isobornane, tricyclodecane, and tetracyclododecane. Of these hydrocarbon rings, adamantane, norbornane, tricyclodecane, and tetracyclododecane are preferred, and adamantane is particularly preferred.

These basic rings may include a substituent group on the ring.

Examples of the substituent group include a lower alkyl group, a fluorine atom, a fluorinated lower alkyl group, and an oxygen atom (=O). Examples of the lower alkyl group include straight-chained or branched-chained alkyl groups of 1 to 5 carbon atoms, such as a methyl group and an ethyl group. When the basic ring has a substituent group, the number of the substituent groups is preferably from 1 to 3, and more preferably 1. Herein, the expression "includes a substituent group" means that hydrogen atoms bonded to carbon atoms that form a basic ring are substituted with a substituent group.

The cyclic alkyl group as $R_1$ includes a group in which one hydrogen atom has been removed from these basic rings. In $R_1$, the carbon atom bonded to an adjacent oxygen atom of $R_1$ is preferably one of the carbon atoms that form the above basic ring is preferred, and the carbon atom bonded to an adjacent oxygen atom of $R_1$ is particularly preferably a tertiary carbon atom bonded with a substituent group such as a lower alkyl group, in terms of achieving excellent effects for the present invention.

Examples of acid dissociable, dissolution inhibiting groups containing a cyclic alkyl group as $R_1$ include groups represented by the formula (P1-1) shown below:

[Chemical formula 6]

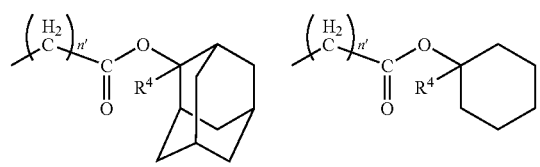

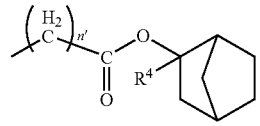

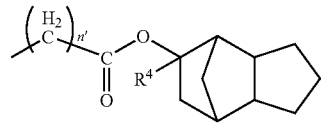

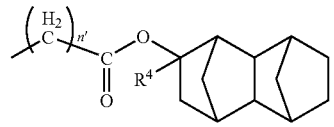

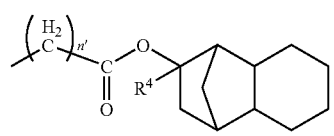

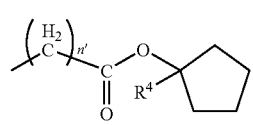

[wherein, $R^4$ represents a lower alkyl group, and n' is as defined above].

Of these groups, those represented by the general formula (P1-2) shown below are preferred:

[Chemical formula 7]

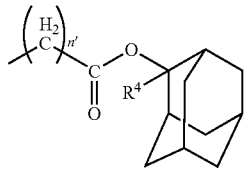
(P1-2)

[wherein, $R^4$ represents a lower alkyl group, and n' is as defined above].

The lower alkyl group as $R^4$ is an alkyl group of 1 to 5 carbon atoms, and specific examples include lower straight-chained or branched-chained alkyl groups such as a methyl group, an ethyl group, a propyl group, an isopropyl group, an n-butyl group, an isobutyl group, a tert-butyl group, a pentyl group, an isopentyl group, and a neopentyl group. $R^4$ is preferably a methyl group or an ethyl group, and more preferably a methyl group, in terms of factors such as industrial availability.

In the formula (p2), $R^2$ includes the same groups as those of $R^1$. Of these groups, $R^2$ is preferably a straight-chained alkyl group or a cyclic alkyl group.

$R^3$ is a hydrogen atom or a lower alkyl group. The lower alkyl group as $R^3$ is an alkyl group of 1 to 5 carbon atoms, and specific examples include lower straight-chained or branched-chained alkyl groups such as a methyl group, an ethyl group, a propyl group, an isopropyl group, an n-butyl group, an isobutyl group, a tert-butyl group, a pentyl group, an isopentyl group, and a neopentyl group. $R^3$ is preferably a hydrogen atom or a methyl group, and more preferably a hydrogen atom, in terms of factors such as industrial availability.

Examples of the group represented by formula (p2) in which $R^2$ is a straight-chained alkyl group include a 1-ethoxyethyl group, a 1-ethoxymethyl group, a 1-methoxyethyl group, a 1-methoxymethyl group, a 1-methoxypropyl group, a 1-ethoxypropyl group, a 1-n-butoxyethyl group, a 1-pentafluoroethoxyethyl group, a 1-trifluoromethoxyethyl group, and a 1-trifluoromethoxymethyl group.

Examples of the group represented by formula (p2) in which $R^2$ is a cyclic alkyl group include groups represented by the formula (P2-1) shown below:

[Chemical formula 8]

(P2-1)

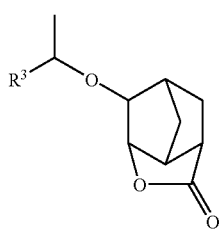 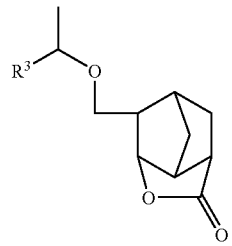

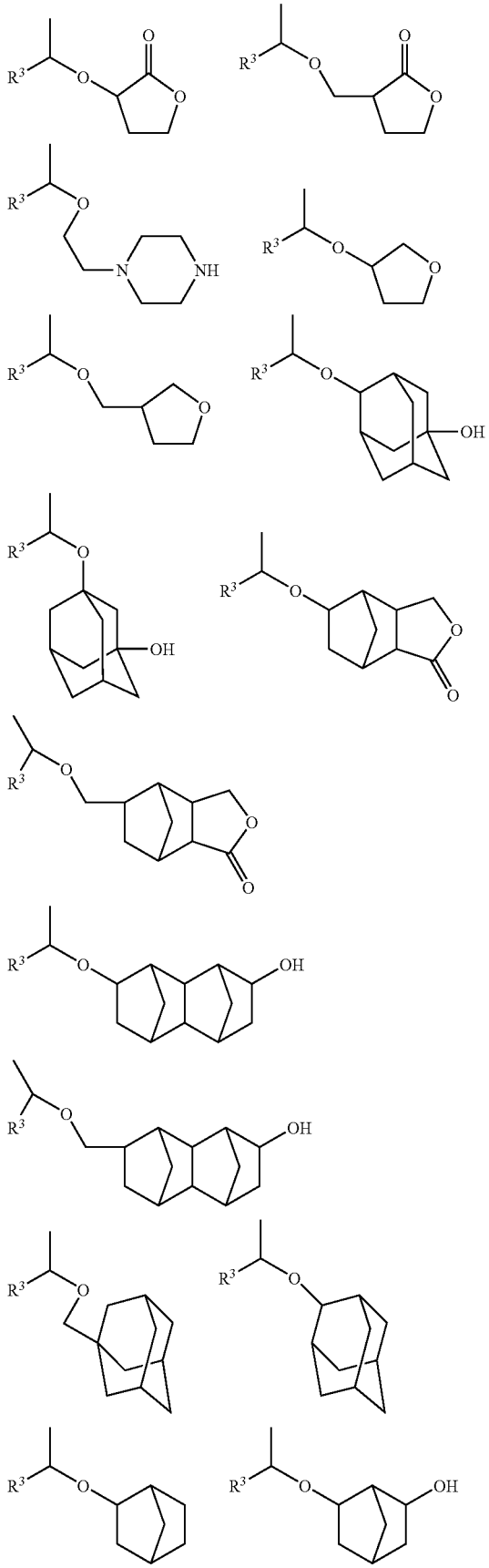

-continued

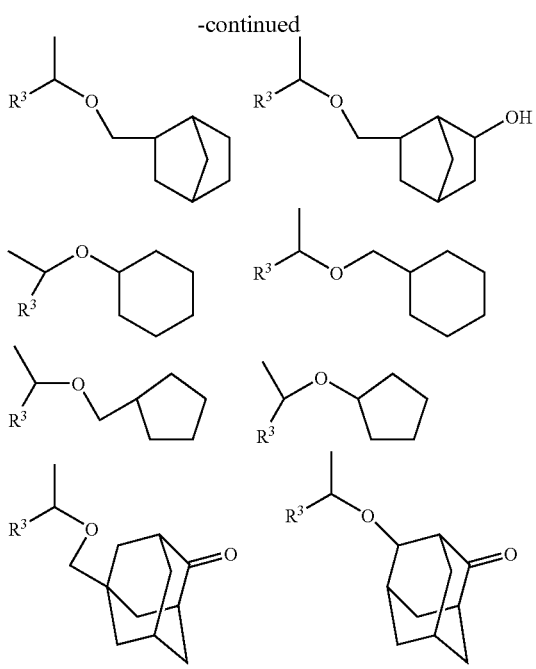

[wherein, $R^3$ is as defined above].

Preferred groups are those represented by the general formula (P2-2) shown below:

[Chemical Formula 9]

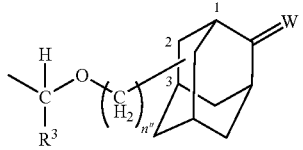

(P2-2)

[wherein, $R^3$ is as defined above, n" represents an integer of 0, 1 or 2, and W represents two hydrogen atoms or oxygen atoms].

n" is most preferably 0 or 1. There are no particular restrictions on the bonding position between an adamantyl group and —C($R_3$)—O—(CH$_2$)$_{n''}$—, and it is preferred to bond to either position 1 or position 2 of the adamantyl group.

In a compound (A1), there are no particular restrictions on which two of the group of $R^{21}$ to $R^{24}$ represent acid dissociable, dissolution inhibiting groups. A compound (A1) may be a mixture of plural structural isomers whose binding positions at acid dissociable, dissolution inhibiting groups are different from each other.

Specific examples of the structural isomer include a structural isomer which has two acid dissociable, dissolution inhibiting groups at one side in view of X in general formula (I) (a structural isomer in which $R^{21}$ and $R^{22}$ represent acid dissociable, dissolution inhibiting groups and the others represent hydrogen atoms, and $R^{23}$ and $R^{24}$ represent acid dissociable, dissolution inhibiting groups and the others represent hydrogen atoms) and a structural isomer which has an acid dissociable, dissolution inhibiting group each at both sides in view of X in general formula (I) (a structural isomer in which $R^{21}$ and $R^{23}$ represent acid dissociable, dissolution inhibiting groups and the others represent hydrogen atoms, and $R^{22}$ and $R^{24}$ represent acid dissociable, dissolution inhibiting groups and the others represent hydrogen atoms).

The compound (A1) is especially preferably a compound (A1-1) represented by a general formula (II) below.

[Chemical formula 10]

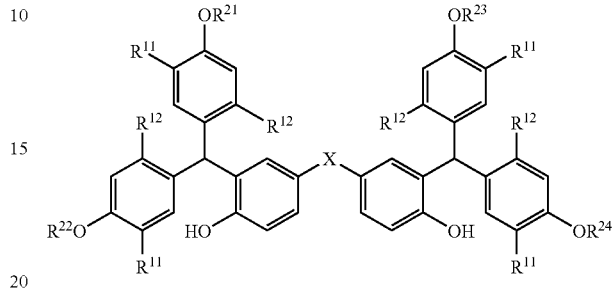

(II)

[wherein, in the general formula (II), $R^{11}$ to $R^{12}$, $R^{21}$ to $R^{24}$ and X are as defined above].

For example, the compound (A1) can be produced as follows.

Firstly, with respect to a polyphenol compound (a) in which all of the group of $R^{21}$ to $R^{24}$ in the general formula (I) represent hydrogen atoms, a hydrogen atom in the phenolic hydroxyl group is substituted with an acid dissociable, dissolution inhibiting group using a known method (for example, a polyphenol compound (a) is reacted with a compound which is represented by the formula X-Y [wherein, X represents a halogen atom such as a bromine atom and a chlorine atom; Y represents an acid dissociable, dissolution inhibiting group.]), thereby, a mixture of a compound is obtained in which a portion of, or all of, the hydrogen atoms within the phenolic hydroxyl group have been substituted with an acid dissociable, dissolution inhibiting group.

Thereafter, a compound other than the compound in which two of the group of $R^{21}$ to $R^{24}$ are substituted with an acid dissociable, dissolution inhibiting group can be obtained through purification and removal using a known method such as liquid chromatography or molecular weight fractionation treatment.

The polyphenol compound (a) can be synthesized, for example, by dissolving a bissalicylaldehyde derivative and a phenol derivative (in an amount of about 4 equivalents based on the bissalicylaldehyde derivative) in an organic solvent and reacting under acidic conditions.

The polyphenol compound (a) preferably has a molecular weight within a range from 300 to 2,500, more preferably from 450 to 1,500, and the most preferably from 500 to 1,200. When the molecular weight is the upper limit or less, in the case where the component (A1) is used in the resist composition, the roughness is reduced and the pattern shape is further improved, and also the resolution is improved. In contrast, when the molecular weight is the lower limit or more, a resist pattern having a good profile shape can be formed.

The polyphenol compound (a) is a material which can form an amorphous film by a spin coating method. As used herein, amorphous film means a non-crystallizable and optically transparent film. The spin coating method is one of usually used thin film forming methods.

It is possible to discriminate whether or not a polyphenol compound can form an amorphous film using a spin coating method by confirming whether or not the entire coating film formed on an 8 inch silicone wafer using a spin coating method is transparent. More specifically, discrimination can be performed as follows. First, the polyphenol material is mixed in a mixed solvent having a concentration of 14 mass %, which is prepared by using solvents used usually in a resist solvent, for example, ethyl lactate and propylene glycol monomethyl ether acetate (mass ratio: 40/60) (hereinafter abbreviated to EM), by subjecting to an ultrasonic treatment (dissolution treatment) using an ultrasonic cleaner. The solution is spin-coated on a wafer at 1,500 rpm and then optionally baked dry (PAB, Post Applied Bake) under the conditions of a temperature of 110° C. for 90 seconds. It is confirmed whether or not an amorphous film is formed by visually observing the transparency of the film. An opaque film, which is not transparent, is not the amorphous film.

In the present invention, the polyphenol compound (a) is preferably an amorphous film having excellent stability, for example, an amorphous state is maintained even after the film is allowed to stand under a room temperature environment for 2 weeks after PAB.

The compound (A1) stated above in the present application is a compound in which two within the specific four phenolic hydroxyl groups are protected with an acid dissociable, dissolution inhibiting group of six phenolic hydroxyl groups in the polyphenol compound (a) in which all of the group of $R^{21}$ to $R^{24}$ represent hydrogen atoms in the formula (I), and whose number of protective groups is 2.

Herein, the term "the number of protective groups" means the number of phenolic hydroxyl groups protected with acid dissociable, dissolution inhibiting groups in the compound (A1).

For example, the number of protective groups can be determined by the following procedure. A protection ratio (%) is measured by NMR (nuclear magnetic resonance spectrum) such as proton-NMR or carbon NMR and the number of protective groups is determined from the value and the structure of the polyphenol compound (a).

Herein, the term "protection ratio" means the proportion (mol %) of the number of protective groups based on the total of the number of phenolic hydroxyl groups protected with acid dissociable, dissolution inhibiting groups (i.e., the number of protective groups) and the number of non-protected phenolic hydroxyl groups in the compound (A1).

The present application can provide a resist pattern having reduced roughness by using the compound (a1).

The reasons for this are as follows. Although the compound (A1) has a structure in which two within the four specific phenolic hydroxyl groups are protected with an acid dissociable, dissolution inhibiting group in the specific structure of the polyphenol compound as stated above, multiple molecules each containing a different number of protective groups, are usually produced during the synthesis reaction. That is, not only the compound (A1) but also a mixture including multiple molecules, each containing a different number of protective groups is usually produced after the synthesis. Thus, there is a fluctuation in the number of the acid dissociable, dissolution inhibiting groups within each molecule and a difference in the characteristics within each molecule, that is, for example, a difference in the alkali solubility. Therefore, the resist film obtained using the mixture has unevenness, for example, in the distribution of various components in the film, alkali solubility, and thermal properties (Tg (glass transition point)), and thus the roughness is assumed to be worsened.

In contrast, in the present invention, the resist pattern whose roughness is reduced is supposed to be formed using the compound in which the specific two hydroxyl groups are protected and whose number of protective groups is 2 alone since the difference in properties with the molecule, for example, alkali solubility do not vary or vary very little.

<<A Positive Resist Composition>>

The positive resist composition in the present invention includes a base material component (A) which exhibits increased alkali solubility under action of acid (hereafter also referred to as a component (A)) and an acid generator component (B) that generates acid upon exposure (hereafter also referred to as a component (B)).

In the component (A), the action of the acid generated from the component (B) upon exposure causes the acid-dissociable, dissolution-inhibiting groups to dissociate, causing the entire component (A) to change from an alkali-insoluble state to an alkali-soluble state. As a result, when a resist film formed from the resist composition is selectively exposed during the formation of a resist pattern, or alternatively is exposed and then subjected to post exposure baking, the exposed portions of the resist shift to an alkali-soluble state, whereas the unexposed portions remain insoluble in alkali, meaning alkali developing can then be used to form a positive resist pattern.

<Component (A)>

The positive resist composition in the present invention must have a compound (A1) as the component (A) in the present invention stated above. Herein, when the component (A) is the compound (A1), the positive resist composition in the present invention does not include a base material component which exhibits increased alkali solubility under action of acid other than the compound (A1) as the component (A).

In the component (A), the compound (A1) may be used alone, or a combination of two or more different compounds may be used.

The content of the component (A) in the positive resist composition of the present invention may be adjusted according to the thickness of the resist film to be formed.

<Component (B)>

There are no particular restrictions on the component (B) and it is possible to use those which have conventionally been proposed as an acid generator for a chemically amplified resist. As the acid generator, there are known various acid generators, for example, onium salt-based acid generators such as an iodonium salt and a sulfonium salt, oxime sulfonate-based acid generators, diazomethane-based acid generators such as bisalkyl or bisarylsulfonyldiazomethanes and poly(bissulfonyl)diazomethanes, nitrobenzylsulfonate-based acid generators, iminosulfonate-based acid generators, and disulfone-based acid generators.

Examples of the onium salt-based acid generators include acid generators represented by general formula (b-0):

(b-0)

[Chemical formula 11]

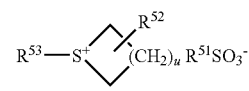

[wherein, $R^{51}$ represents a straight-chained, branched-chained or cyclic alkyl group, or a straight-chained, branched-chained or cyclic fluorinated alkyl group; $R^{52}$ represents a hydrogen atom, a hydroxyl group, a halogen atom, a straight-chained or branched-chained alkyl group, a straight-chained or branched-chained halogenated alkyl group, or a straight-chained or branched-chained alkoxy group; $R^{53}$ represents an aryl group which may have a substituent group; u represents an integer from 1 to 3].

In the general formula (b-0), $R^{51}$ represents a straight-chained, branched-chained or cyclic alkyl group, or a straight-chained, branched-chained or cyclic fluorinated alkyl group.

The straight-chained or branched-chained alkyl group has preferably 1 to 10 carbon atoms, more preferably 1 to 8, the most preferably 1 to 4 carbon atoms.

The cyclic alkyl group has preferably 4 to 12 carbon atoms, more preferably 5 to 10 carbon atoms, the most preferably 6 to 10 carbon atoms.

The fluorinated alkyl group has preferably 1 to 10 carbon atoms, more preferably 1 to 8 carbon atoms, the most preferably 1 to 4. Furthermore, the fluorination rate of the fluorinated alkyl group (the proportion of the fluorine atoms in the alkyl group) is preferably 10 to 100%, more preferably 50 to 100%, and particularly those in which all of the hydrogen atoms have been substituted with fluorine atoms, thus giving strong acidity, are preferred.

$R^{51}$ is most preferably a straight-chained alkyl group or a straight-chained fluorinated alkyl group.

$R^{52}$ is a hydrogen atom, a hydroxyl group, a halogen atom, a straight-chained, branched-chained or cyclic alkyl group, a straight-chained or branched-chained halogenated alkyl group, or a straight-chained or branched-chained alkoxy group.

Examples of the halogen atom as $R^{52}$ include a fluorine atom, a bromine atom, a chlorine atom, and an iodine atom, and among these, a fluorine atom is preferred.

When the alkyl group as $R^{52}$ is straight-chained or branched-chained, the straight-chained or branched-chained alkyl group preferably has 1 to 5 carbon atoms, more preferably 1 to 4 carbon atoms, and still more preferably 1 to 3 carbon atoms. Moreover, when the alkyl group as $R^{52}$ is cyclic, the cyclic alkyl group preferably has 4 to 12 carbon atoms, more preferably 5 to 10 carbon atoms, and still more preferably 6 to 10 carbon atoms. The halogenated alkyl group as $R^{52}$ is a group in which a part or all of the hydrogen atoms of the alkyl group have been substituted with halogen atoms. Here, examples of the alkyl group include the same "alkyl groups" mentioned above as $R^{52}$. Examples of the substituting halogen atoms include the same as those mentioned above in the description of the "halogen atom". For the halogenated alkyl group, it is preferable that 50 to 100% of the total hydrogen atoms be substituted with halogen atoms, and it is more preferable that 100% of the total hydrogen atoms be substituted with halogen atoms.

The alkoxy group as $R^{52}$ is straight-chained or branched-chained, and preferably it has 1 to 5 carbon atoms, more preferably 1 to 4 carbon atoms, and still more preferably 1 to 3 carbon atoms.

Among these, a hydrogen atom is preferred as $R^{52}$.

$R^{53}$ is an aryl group that may have a substituent group and preferably 6 to 15 carbon atoms, and examples of the structure of its basic ring in which the substituent group is excluded (a base ring) include a naphthyl group, a phenyl group, and an anthracenyl group, and among these, a phenyl group is preferred, from the viewpoints of the effect of the present invention, or absorption of exposure light of an ArF excimer laser, etc.

Examples of the substituent group include a hydroxyl group, and a lower alkyl group (which is straight-chained or branched-chained, and preferably has 5 or less carbon atoms, and among these, a methyl group is particularly preferred).

The aryl group of $R^{53}$ further preferably has no substituent groups.

u is an integer of 1 to 3, preferably 2 or 3, and particularly preferably 3.

Preferable examples of the acid generator represented by the general formula (b-0) are represented by the chemical formula (b-0-0) below.

[Chemical formula 12]

(b-0-0)

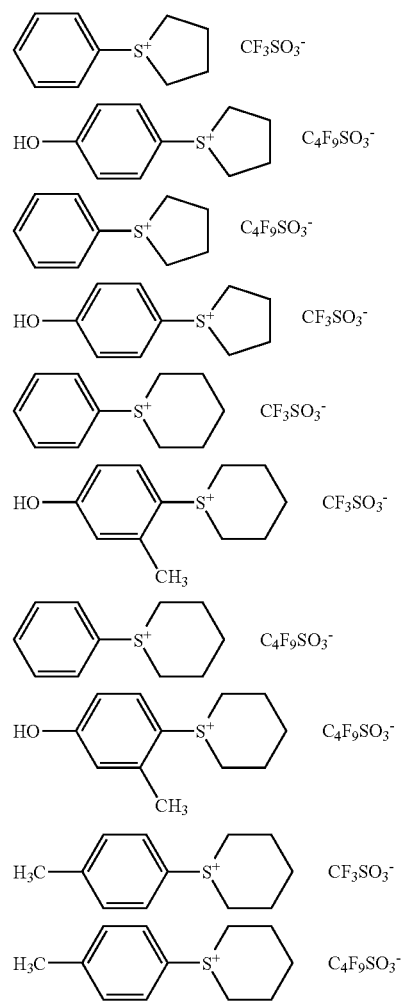

Of these, a compound represented by the general formula (b-0-1) below is preferable.

[Chemical formula 13]

(b-0-1)

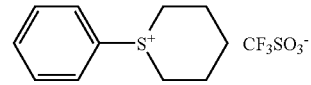

The acid generator represented by the general formula (b-0) can be used alone or as a mixture of two or more.

Examples of the another onium salt-based acid generator in acid generators represented by the general formula (b-0) includes a compound represented by the general formulas (b-1) or (b-2) below.

[Chemical formula 14]

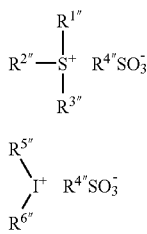

(b-1)

(b-2)

[wherein, $R^{1''}$ to $R^{3''}$, and $R^{5''}$ to $R^{6''}$ each independently represents an aryl group or an alkyl group; $R^{4''}$ represents a straight-chained, branched-chained or cyclic alkyl group, or a fluorinated alkyl group; at least one of $R^{1''}$ to $R^{3''}$ represents an aryl group; and at least of $R^{5''}$ to $R^{6''}$ represents an aryl group.]

In the formula (b-1), $R^{1''}$ to $R^{3''}$ each independently represents an aryl group or an alkyl group. At least one of $R^{1''}$ to $R^{3''}$ represents an aryl group. It is preferable that at least two of $R^{1''}$ to $R^{3''}$ be aryl groups, and it is most preferable that all of $R^{1''}$ to $R^{3''}$ be aryl groups.

The aryl groups of $R^{1''}$ to $R^{3''}$ are not particularly limited, and examples thereof include an aryl group having 6 to 20 carbon atoms. In the aryl group, a part of all of the hydrogen atoms may or may not be substituted with an alkyl group, an alkoxy group, a halogen atom, etc. As the aryl group, an aryl group having 6 to 10 carbon atoms is preferred, in view of inexpensive synthesis. Specific examples thereof include a phenyl group, and a naphthyl group.

As the alkyl group that may substitute the hydrogen atom of the aryl group, an alkyl group having 1 to 5 carbon atoms is preferred, and a methyl group, an ethyl group, a propyl group, an n-butyl group, or a tert-butyl group is most preferred.

As the alkoxy group that may substitute the hydrogen atom of the aryl group, an alkoxy group having 1 to 5 carbon atoms is preferred, and a methoxy group or an ethoxy group is most preferred.

As the halogen atom that may substitute the hydrogen atom of the aryl group, a fluorine atom is preferred.

The alkyl group of $R^{1''}$ to $R^{3''}$ is not particularly limited, and examples thereof include a straight-chained or branched-chained alkyl group having 1 to 10 carbon atoms, or a cyclic alkyl group having 4 to 15 carbon atoms, preferably 4 to 10 carbon atoms, more preferably 6 to 10 carbon atoms. It is preferable that the alkyl group have 1 to 5 carbon atoms, in view of excellent resolution. Specific examples thereof include a methyl group, an ethyl group, an n-propyl group, an isopropyl group, an n-butyl group, an isobutyl group, an n-pentyl group, a cyclopentyl group, a hexyl group, a cyclohexyl group, a nonyl group, and a decanyl group, and among these, a methyl group is preferred, in view of excellent resolution and inexpensive synthesis.

Among these, it is most preferred that each of $R^{1''}$ to $R^{3''}$ be a phenyl group.

$R^{4''}$ represents a straight-chained, branched-chained or cyclic alkyl group or fluorinated alkyl group.

The straight-chained or branched-chained alkyl group preferably has 1 to 10 carbon atoms, more preferably 1 to 8 carbon atoms, and most preferably 1 to 4 carbon atoms.

The cyclic alkyl group is a cyclic group represented by $R^{1''}$ above having preferably 4 to 15 carbon atoms, more preferably 4 to 10 carbon atoms, and most preferably 6 to 10 carbon atoms.

The fluorinated alkyl group preferably has 1 to 10 carbon atoms, more preferably 1 to 8 carbon atoms, and most preferably 1 to 4 carbon atoms. The fluorination rate of the fluorinated alkyl group (the proportion of the fluorine atoms in the alkyl group) is preferably 10 to 100%, still more preferably 50 to 100%, and particularly those in which all of the hydrogen atoms have been substituted with fluorine atoms, thus giving strong acidity, are preferred.

As $R^{4''}$, a straight-chained or cyclic alkyl group, or a fluorinated alkyl group is most preferred.

In the formula (b-2), $R^{5''}$ to $R^{6''}$ each independently represents an aryl group or an alkyl group. At least one of $R^{5''}$ to $R^{6''}$ represents an aryl group. Preferably, all of $R^{5''}$ to $R^{6''}$ are aryl groups.

Examples of the aryl group of $R^{5''}$ to $R^{6''}$ include the same as those mentioned for the aryl group of $R^{1''}$ to $R^{3''}$.

Examples of the alkyl group of $R^{5''}$ to $R^{6''}$ include the same as those mentioned for the alkyl group of $R^{1''}$ to $R^{3''}$.

Among these, it is most preferable that all of $R^{5''}$ to $R^{6''}$ be phenyl groups.

Examples of $R^{4''}$ in the formula (b-2) include the same as those mentioned for $R^{4''}$ in the formula (b-1).

Specific examples of the onium salt-based acid generator represented by the formulas (b-1) or (b-2) include diphenyliodonium trifluoromethanesulfonate or nonafluorobutanesulfonate, bis(4-tert-butylphenyl) iodonium trifluoromethanesulfonate or nonafluorobutanesulfonate, triphenylsulfonium trifluoromethanesulfonate, heptafluoropropanesulfonate or nonafluorobutanesulfonate, tri(4-methylphenyl) sulfonium trifluoromethanesulfonate, heptafluoropropanesulfonate or nonafluorobutanesulfonate, dimethyl(4-hydroxynaphthyl) sulfonium trifluoromethanesulfonate, heptafluoropropanesulfonate or nonafluorobutanesulfonate, monophenyldimethylsulfonium trifluoromethanesulfonate, heptafluoropropanesulfonate or nonafluorobutanesulfonate, diphenylmonomethylsulfonium trifluoromethanesulfonate, heptafluoropropanesulfonate or nonafluorobutanesulfonate, (4-methyl phenyl) diphenylsulfonium trifluoromethanesulfonate, heptafluoropropanesulfonate or nonafluorobutanesulfonate, (4-methoxyphenyl) diphenylsulfonium trifluoromethanesulfonate, heptafluoropropanesulfonate or nonafluorobutanesulfonate, tri(4-tert-butyl)phenylsulfonium trifluoromethanesulfonate, heptafluoropropanesulfonate or nonafluorobutanesulfonate, diphenyl(1-(4-methoxy)naphthyl) sulfonium trifluoromethanesulfonate, heptafluoropropanesulfonate or nonafluorobutanesulfonate, di(1-naphthyl) phenylsulfonium trifluoromethanesulfonate, heptafluoropropanesulfonate or nonafluorobutanesulfonate, and the like. Also, the onium salts in which the anionic part has been substituted with methanesulfonate, n-propanesulfonate, n-butanesulfonate, or n-octanesulfonate can be used.

Further, in the general formulas (b-1) or (b-2), the onium salt-based acid generator in which in the anionic part has been substituted with the anionic part represented by the following general formulas (b-3) or (b-4) can also be used (the cationic part is the same as for (b-1) or (b-2)).

[Chemical Formula 15]

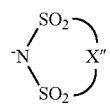

(b-3)

-continued

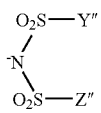
(b-4)

[wherein, X" represents an alkylene group having 2 to 6 carbon atoms in which at least one hydrogen atom has been substituted with a fluorine atom; and Y" and Z" each independently represents an alkyl group having 1 to 10 carbon atoms in which at least one hydrogen atom has been substituted with a fluorine atom].

X" is a straight-chained or branched-chained alkylene group in which at least one hydrogen atom has been substituted with a fluorine atom, and the alkylene group has 2 to 6 carbon atoms, preferably 3 to 5 carbon atoms, and most preferably 3 carbon atoms.

Y" and Z" are each independently a straight-chained or branched-chained alkyl group in which at least one hydrogen atom has been substituted with a fluorine atom, and the alkyl group has 1 to 10 carbon atoms, preferably 1 to 7 carbon atoms, and most preferably 1 to 3 carbon atoms.

It is preferable that the alkylene group of X", or of the alkyl group of Y" and Z" have a smaller number of carbon atoms within the above-described range, in view of good solubility in a resist solvent.

Further, it is preferable that the alkylene group of X", or the alkyl group of Y" and Z" have a that larger number of the hydrogen atoms substituted with fluorine atoms in view of stronger acidity, and higher transparency to an electron beam or a high-energy light at 200 nm or less. The proportion of the fluorine atoms in the alkylene group or alkyl group, that is, the fluorination rate is preferably 70 to 100%, still more preferably 90 to 100%, and a perfluoroalkylene group or perfluoroalkyl group in which all of the hydrogen atoms are substituted with fluorine atoms, is particularly preferred.

As used in the present invention, the oxime sulfonate-based acid generator is a compound having at least one group represented by the following general formula (B-1), which is characterized by generation of an acid upon irradiation with radiation. The oxime sulfonate-based acid generator is widely used for a chemically amplified resist composition, and thus can be optionally selected and used.

[Chemical formula 16]

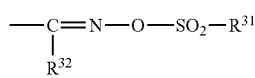
(B-1)

[wherein, in the formula (B-1), $R^{31}$ and $R^{32}$ each independently represents an organic group.]

The organic group of the present invention is a carbon atom-containing group, and may contain atoms other than the carbon atom (for example, a hydrogen atom, an oxygen atom, a nitrogen atom, a sulfur atom, and a halogen atom (such as a fluorine atom, and a chlorine atom)).

The organic group of $R^{31}$ is preferably a straight-chained, branched-chained, or cyclic alkyl group or an aryl group. The alkyl group or the aryl group may have a substituent group. The substituent group is not particularly limited, and examples thereof include a fluorine atom, and a straight-chained, branched-chained, or cyclic alkyl group having 1 to 6 carbon atoms. As used herein, the expression "having a substituent group" means that a part or all of the hydrogen atoms of the alkyl group or the aryl group are substituted with substituent groups.

The alkyl group preferably has 1 to 20 carbon atoms, more preferably 1 to 10 carbon atoms, still more preferably 1 to 8 carbon atoms, particularly preferably 1 to 6 carbon atoms, and most preferably 1 to 4 carbon atoms. The alkyl group is particularly preferably a partially or completely halogenated alkyl group (sometimes referred to as a halogenated alkyl group, hereinafter). The partially halogenated alkyl group refers to an alkyl group in which a part of the hydrogen atoms are substituted with halogen atoms, and the completely halogenated alkyl group refers to an alkyl group in which all of the hydrogen atoms are substituted with halogen atoms. Examples of the halogen atom include a fluorine atom, a chlorine atom, a bromine atom, and an iodine atom. It is particularly preferably a fluorine atom. That is, the halogenated alkyl group is preferably a fluorinated alkyl group.

The aryl group preferably has 4 to 20 carbon atoms, more preferably 4 to 10 carbon atoms, and most preferably 6 to 10 carbon atoms. The aryl group is particularly preferably a partially or completely halogenated aryl group. Further, the partially halogenated aryl group refers to an aryl group in which a part of the hydrogen atoms are substituted with halogen atoms, and the completely halogenated aryl group refers to an aryl group in which all of the hydrogen atoms are substituted with halogen atoms.

$R^{31}$ is particularly preferably an unsubstituted alkyl group having 1 to 4 carbon atoms, or a fluorinated alkyl group having 1 to 4 carbon atoms.

The organic group of $R^{32}$ is preferably a straight-chained, branched-chained, or cyclic alkyl group, an aryl group, or a cyano group. Examples of the alkyl group and the aryl group of $R^{32}$ include those as mentioned for the alkyl group and the aryl group of $R^{31}$.

As $R^{32}$, a cyano group, an unsubstituted alkyl group having 1 to 8 carbon atoms, or a fluorinated alkyl group having 1 to 8 carbon atoms is particularly preferred.

More preferable examples of the oxime sulfonate-based acid generator include a compound represented by the following general formulas (B-2) or (B-3).

[Chemical formula 17]

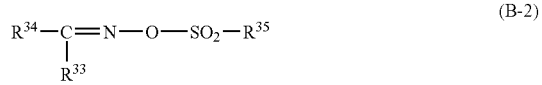
(B-2)

[wherein, in the formula (B-2), $R^{33}$ is a cyano group, an unsubstituted alkyl group, or a halogenated alkyl group; $R^{34}$ is an aryl group; and $R^{35}$ is an unsubstituted alkyl group or a halogenated alkyl group.]

[Chemical formula 18]

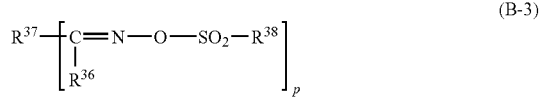
(B-3)

[wherein, in the formula (B-3), $R^{36}$ is a cyano group, an unsubstituted alkyl group, or a halogenated alkyl group; $R^{37}$ is an aromatic di-valent or tri-valent hydrocarbon; $R^{38}$ is an unsubstituted alkyl group, or a halogenated alkyl group; and p is 2 or 3.]

In the general formula (B-2) above, the unsubstituted alkyl group or the halogenated alkyl group of $R^{33}$ preferably has 1 to 10 carbon atoms, more preferably 1 to 8 carbon atoms, and most preferably 1 to 6 carbon atoms.

$R^{33}$ is preferably a halogenated alkyl group, and more preferably a fluorinated alkyl group.

The fluorinated alkyl group of $R^{33}$ is preferably one in which 50% or more of the hydrogen atoms of the alkyl group are fluorinated, more preferably one in which 70% or more of the hydrogen atoms of the alkyl group are fluorinated, and most preferably one in which 90% or more of the hydrogen atoms of the alkyl group are fluorinated.

Examples of the aryl group of $R^{34}$ include a group in which one hydrogen atom has been removed from the ring of an aromatic hydrocarbon such as a phenyl group, a biphenylyl group, a fluorenyl group, a naphthyl group, an anthracyl group, and a phenanthryl group; and a heteroaryl group in which a part of the oxygen atoms constituting those rings are substituted with heteroatoms such as an oxygen atom, a sulfur atom, and a nitrogen atom. Among these, a fluorenyl group is preferred.

The aryl group of $R^{34}$ may have a substituent group such as an alkyl group having 1 to 10 carbon atoms, a halogenated alkyl group, and an alkoxy group. The alkyl group or the halogenated alkyl group as the substituent group preferably has 1 to 8 carbon atoms, and more preferably 1 to 4 carbon atoms. Further, the halogenated alkyl group is preferably a fluorinated alkyl group.

The unsubstituted alkyl group or the halogenated alkyl group of $R^{35}$ preferably has 1 to 10 carbon atoms, more preferably 1 to 8 carbon atoms, and most preferably 1 to 6 carbon atoms.

$R^{35}$ is preferably a halogenated alkyl group, more preferably a fluorinated alkyl group, and most preferably a partially fluorinated alkyl group.

The fluorinated alkyl group of $R^{35}$ is preferably one in which 50% or more of the hydrogen atoms of the alkyl group are fluorinated, more preferably one in which 70% or more of the hydrogen atoms of the alkyl group are fluorinated, and most preferably one in which 90% or more of the hydrogen atoms of the alkyl group are fluorinated, thus giving higher acidity of an acid generated. Most preferably, it is one in which 100% of the hydrogen atoms of the alkyl group are completely fluorinated.

In the general formula (B3-3), examples of the unsubstituted alkyl group or the halogenated alkyl group of $R^{36}$ include the same as the unsubstituted alkyl group or the halogenated alkyl group of $R^{33}$.

Examples of the aromatic di-valent or tri-valent hydrocarbon group of $R^{37}$ include a group in which one or two hydrogen atoms have been removed from the aryl group of $R^{34}$.

Examples of the unsubstituted alkyl group or the halogenated alkyl group of $R^{38}$ include the same as those described above for the unsubstituted alkyl group or the halogenated alkyl group of $R^{35}$. p is preferably 2.

Specific examples of the oxime sulfonate-based acid generator include

α-(p-toluenesulfonyloxyimino)-benzylcyanide,
α-(p-chlorobenzenesulfonyloxyimino)-benzylcyanide,
α-(4-nitrobenzenesulfonyloxyimino)-benzylcyanide,
α-(4-nitro-2-trifluoromethylbenzenesulfonyloxyimino)-benzylcyanide,
α-(benzenesulfonyloxyimino)-4-chlorobenzylcyanide,
α-(benzenesulfonyloxyimino)-2,4-dichlorobenzylcyanide,
α-(benzenesulfonyloxyimino)-2,6-dichlorobenzylcyanide,
α-(benzenesulfonyloxyimino)-4-methoxybenzylcyanide,
α-(2-chlorobenzenesulfonyloxyimino)-4-methoxybenzylcyanide,
α-(benzenesulfonyloxyimino)-thien-2-ylacetonitrile,
α-(4-dodecylbenzenesulfonyloxyimino)-benzylcyanide,
α-[(p-toluenesulfonyloxyimino)-4-methoxyphenyl]acetonitrile,
α-[(dodecylbenzenesulfonyloxyimino)-4-methoxyphenyl]acetonitrile,
α-(tosyloxyimino)-4-thienylcyanide,
α-(methylsulfonyloxyimino)-1-cyclopentenylacetonitrile,
α-(methylsulfonyloxyimino)-1-cyclohexenylacetonitrile,
α-(methylsulfonyloxyimino)-1-cycloheptenylacetonitrile,
α-(methylsulfonyloxyimino)-1-cyclooctenylacetonitrile,
α-(trifluoromethylsulfonyloxyimino)-1-cyclopentenylacetonitrile,
α-(trifluoromethylsulfonyloxyimino)-cyclohexylacetonitrile,
α-(ethylsulfonyloxyimino)-ethylacetonitrile,
α-(propylsulfonyloxyimino)-propylacetonitrile,
α-(cyclohexylsulfonyloxyimino)-cyclopentylacetonitrile,
α-(cyclohexylsulfonyloxyimino)-cyclohexylacetonitrile,
α-(cyclohexylsulfonyloxyimino)-1-cyclopentenylacetonitrile,
α-(ethylsulfonyloxyimino)-1-cyclopentenylacetonitrile,
α-(isopropylsulfonyloxyimino)-1-cyclopentenylacetonitrile,
α-(n-butylsulfonyloxyimino)-11-cyclopentenylacetonitrile,
α-(ethylsulfonyloxyimino)-1-cyclohexenylacetonitrile,
α-(isopropylsulfonyloxyimino)-1-cyclohexenylacetonitrile,
α-(n-butylsulfonyloxyimino)-1-cyclohexenylacetonitrile,
α-(methylsulfonyloxyimino)-phenylacetonitrile,
α-(methylsulfonyloxyimino)-p-methoxyphenylacetonitrile,
α-(trifluoromethylsulfonyloxyimino)-phenylacetonitrile,
α-(trifluoromethylsulfonyloxyimino)-p-methoxyphenylacetonitrile,
α-(ethylsulfonyloxyimino)-p-methoxyphenylacetonitrile,
α-(propylsulfonyloxyimino)-p-methylphenylacetonitrile, and
α-(methylsulfonyloxyimino)-p-bromophenylacetonitrile.

Further, examples of suitable oxime sulfonate-based acid generator include the following compounds (compound groups (i)) represented by the chemical formula below.

[Chemical formula 19]

(i)

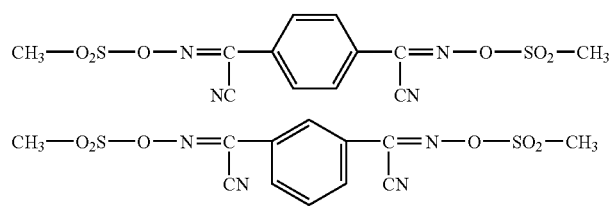

-continued
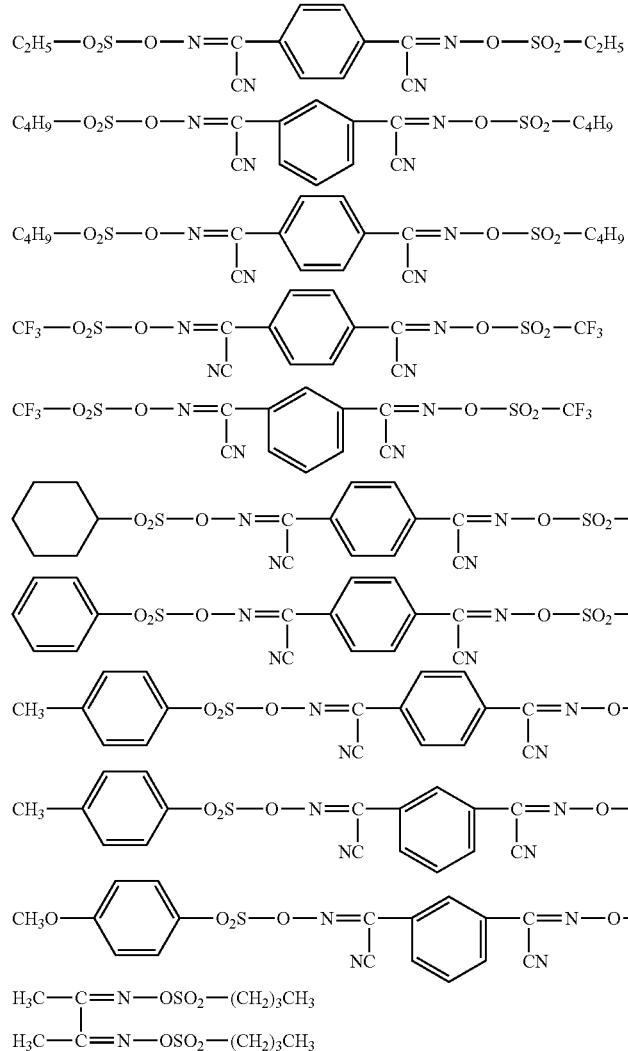
Specific examples of the preferable compounds of the compounds represented by the general formulas (B-2) and (B-3) above (compound groups (ii) and (iii)) are as follows.
[Chemical formula 20]
(ii)
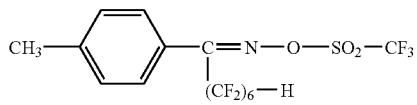
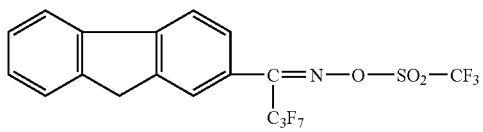
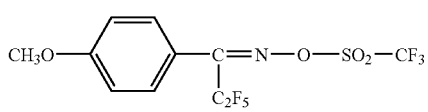
-continued
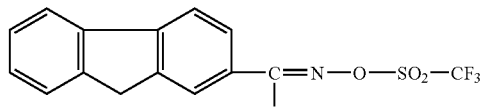
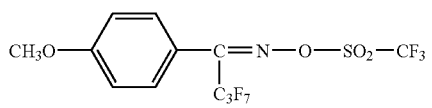
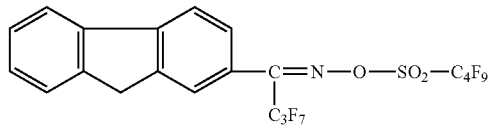
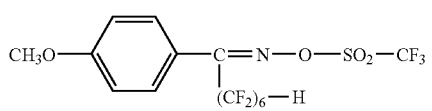

25
-continued
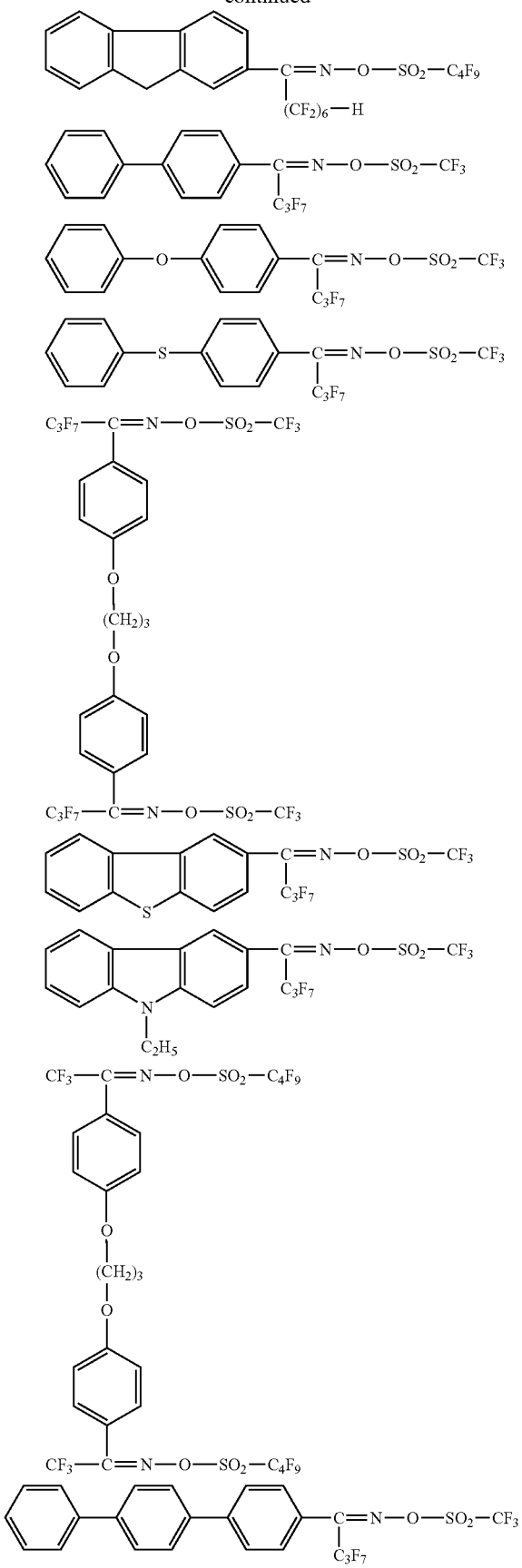
26
-continued
[Chemical formula 21]
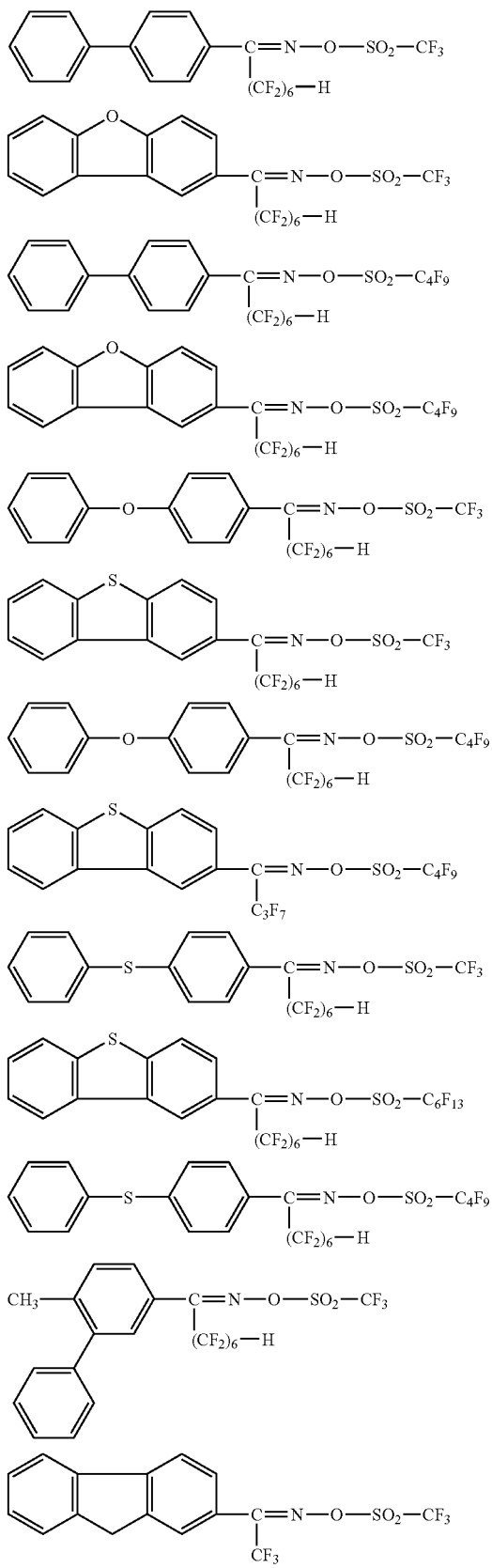

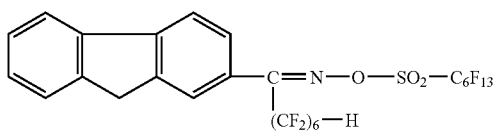

Among the above-exemplified compounds, the following four compounds ((iv) to (vii)) are preferred.

(iv)

[Chemical formula 22]

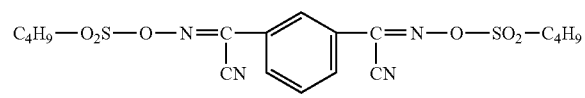

(v)

[Chemical formula 23]

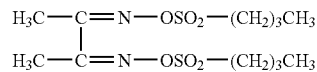

(vi)

[Chemical formula 24]

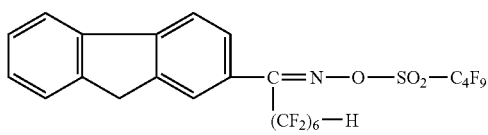

(vii)

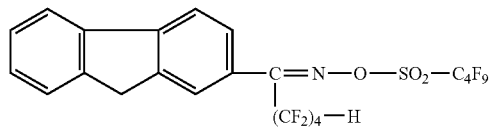

Among the diazomethane-based acid generators, specific examples of bisalkyl or bisarylsulfonyl diazomethanes include bis(isopropylsulfonyl) diazomethane, bis(p-toluenesulfonyl) diazomethane, bis(1,1-dimethylethylsulfonyl) diazomethane, bis(cyclohexylsulfonyl) diazomethane, and bis (2,4-dimethylphenylsulfonyl) diazomethane.

In addition, examples of the poly(bisulfonyl) diazomethanes include 1,3-bis(phenylsulfonyldiazomethylsulfonyl)propane (if A=3), 1,4-bis(phenylsulfonyldiazomethylsulfonyl)butane (if A=4), 1,6-bis(phenylsulfonyldiazomethylsulfonyl)hexane (if A=6), 1,10-bis(phenylsulfonyldiazomethylsulfonyl)decane (if A=10), 1,2-bis(cyclohexylsulfonyldiazomethylsulfonyl)ethane (if B=2), 1,3-bis(cyclohexylsulfonyldiazomethylsulfonyl)propane (if B=3), 1,6-bis(cyclohexylsulfonyldiazomethylsulfonyl)hexane (if B=6), and 1,10-bis(cyclohexylsulfonyldiazomethylsulfonyl)decane (if B=10) which have structures represented by the formulas (viii) and (ix) below.

[Chemical formula 25]

(viii)

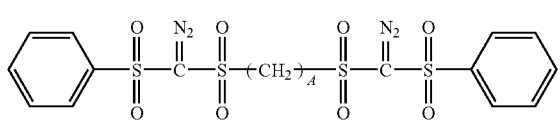

(ix)

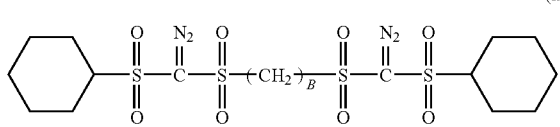

As the component (B), the acid generator may be used alone or in a combination of two or more kinds thereof.

In the present invention, of these, as the component (B), an onium salt having a fluorinated alkylsulfonic acid ion as an anion is preferably used. The content of the component (B) in the positive resist composition of the present invention is 0.5 to 30 parts by weight, and preferably 1 to 15 parts by weight, based on 100 parts by weight of the component (A). If the amount is within the above range, the pattern formation is sufficiently performed. Further, a uniform solution can be obtained, and storage stability is better. Accordingly, the range is considered preferable.

<Optional Components>

In the positive resist composition, in order to improve the resist pattern shape and the post exposure stability of the latent image formed by the pattern-wise exposure of the resist layer, a nitrogen-containing organic compound (D) hereafter referred to as the component (D)) may be added as an optional component.

A multitude of these nitrogen-containing organic compounds have already been proposed, and any of these known compounds can be used, and suitable examples include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine, and tri-n-dodecylamine; and alkyl alcohol amines such as diethanolamine, triethanolamine, diisopropanolamine, triisopropanolamine, di-n-octanolamine, and tri-n-octanolamine. Of these compounds, secondary aliphatic amines and tertiary aliphatic amines are preferred, trialkylamines of 5 to 10 carbon atoms are even more preferred, and tri-n-octylamine is the most desirable.

These compounds may be used either alone, or in combinations of two or more different compounds.

The component (D) is typically used in a quantity within a range from 0.01 to 5.0 parts by weight per 100 parts by weight of the component (A).

Furthermore, in order to prevent any deterioration in sensitivity caused by the addition of the above component (D), and improve the resist pattern shape and the post exposure stability of the latent image formed by the pattern-wise exposure of the resist layer, an organic carboxylic acid, or a phosphorus oxo acid or derivative thereof (E) (hereafter referred to as the component (E)) may also be added to the positive resist composition of the present invention as another optional component. The component (D) and the component (E) can be used in combination, or either one can also be used alone.

Examples of suitable organic carboxylic acids include malonic acid, citric acid, malic acid, succinic acid, benzoic acid, and salicylic acid.

Examples of suitable phosphorus oxo acids or derivatives thereof include phosphoric acid or derivatives thereof such as esters, including phosphoric acid, di-n-butyl phosphate and diphenyl phosphate; phosphonic acid or derivatives thereof such as esters, including phosphonic acid, dimethyl phosphonate, di-n-butyl phosphonate, phenylphosphonic acid, diphenyl phosphonate, and dibenzyl phosphonate; and phosphinic acid or derivatives thereof such as esters, including phosphinic acid and phenylphosphinic acid, and of these, phosphonic acid is particularly preferred.

The component (E) is typically used in a quantity within a range from 0.01 to 5.0 parts by weight per 100 parts by weight of the component (A).

Other miscible additives can also be added to the positive resist composition of the present invention according to need, and examples include additive resins for improving the performance of the resist film, surfactants for improving the coating properties, dissolution inhibitors, plasticizers, stabilizers, colorants, halation prevention agents, and dyes and the like.

<Organic Solvent (S)>

The positive resist composition of the present invention can be prepared by dissolving the materials in an organic solvent (hereinafter referred sometimes to as "component (S)").

The component (S) may be any solvent capable of dissolving the various components used to generate a uniform solution, and one or more solvents selected from known materials used as solvents for conventional chemically amplified resists can be used.

Specific examples of the solvent include lactones such as γ-butyrolactone; ketones such as acetone, methyl ethyl ketone, cyclohexanone, methyl isoamyl ketone, and 2-heptanone; polyhydric alcohols and derivatives thereof, such as ethylene glycol, ethylene glycol monoacetate, diethylene glycol, diethylene glycol monoacetate, propylene glycol, propylene glycol monoacetate, dipropylene glycol, or the monomethyl ether, monoethyl ether, monopropyl ether, monobutyl ether or monophenyl ether of dipropylene glycol monoacetate, and propylene glycol monomethyl ether acetate (PGMEA); cyclic ethers such as dioxane; and esters such as methyl lactate, ethyl lactate (EL), methyl acetate, ethyl acetate, butyl acetate, methyl pyruvate, ethyl pyruvate, methyl methoxypropionate, and ethyl ethoxypropionate.

These organic solvents may be used either alone, or as a mixed solvent of two or more different solvents.

Furthermore, as the component (S), mixed solvents prepared by mixing propylene glycol monomethyl ether acetate (PGMEA) with a polar solvent are preferred. Although the blend ratio (mass ratio) in such mixed solvents can be set in accordance with factors such as the co-solubility of the PGMEA and the polar solvent, the ratio is preferably within a range from 1:9 to 9:1, and is even more preferably from 2:8 to 8:2.

More specifically, in those cases where EL is added as the polar solvent, the mass ratio PGMEA:EL is preferably within a range from 1:9 to 9:1, and is even more preferably from 2:8 to 8:2.

Furthermore, as the component (S), mixed solvents containing at least one of PGMEA and EL, together with γ-butyrolactone, are also preferred. In such cases, the weight ratio of the former and latter components in the mixed solvent is preferably within a range from 70:30 to 95:5.

There are no particular restrictions on the amount used of the component (S), although the amount should be set in accordance with the coating film thickness required, at a concentration that enables favorable application of the solution to a substrate or the like. Typically, the amount of the solvent is set so that the solid fraction concentration of the resist composition falls within a range from 2 to 20% by mass, and preferably from 5 to 15% by weight.

<<A Resist Pattern Forming Method>>

The method for forming a resist pattern of the present invention includes the steps of forming a resist film on a substrate using the positive resist composition according to the second aspect, exposing the resist film, and developing the resist film, thereby forming a resist pattern.

More specifically, a resist pattern can be formed by the following resist pattern forming method. Namely, the above positive resist composition is first applied to a substrate such as a silicon wafer using a spin coater or the like, and post applied prebaking (PAB) is then conducted, thus forming a resist film. The resist film thus formed is selectively exposed by exposure through a mask pattern or by writing with direct irradiation with electron beam through no mask pattern using an exposure apparatus such as electron beam lithography system or EUV exposure apparatus, and then subjected to post exposure baking (PEB). After developing with an alkali developing solution, the developing solution on the substrate and the resist composition dissolved by the developing solution are washed away by a rinsing treatment, followed by drying to obtain a resist pattern.

These steps can be conducted using a known method. Preferably, the operation conditions are appropriately set according to the composition of the positive resist composition to be used and properties.

There are no particular restrictions on the exposure light source, and an ArF excimer laser, a KrF excimer laser, a $F_2$ excimer laser, or other radiation such as EUV (extreme ultraviolet), VUV (vacuum ultraviolet), EB (electron beam), X-ray or soft X-ray radiation can be used. The present invention is particularly effective for use with electron beams or EUV, particularly electron beams.

During the steps, if necessary, a post exposure baking step may also be included after the alkali development.

An organic or inorganic anti-reflective film may also be provided between the substrate and the applied layer of the resist composition.

EXAMPLES

Examples of the present invention will now be described, but the scope of the present invention is not limited to the following Examples.

Preparation Example 1

Preparation of Compound (A)-1

10 g of a polyphenol compound (1) represented by formula (1) shown below (manufactured by Honshu Chemical Industry Co., Ltd.) was dissolved in 50 g of tetrahydrofuran (THF) and 1.12 g of 60 weight % sodium hydride (NaH) was added at 0° C., followed by stirring for 10 minutes, addition of 8.01 g of bromoacetic acid-2-methyl-2-adamantyl represented by formula (5) shown below and further stirring at room temperature (r.t.) for 5 hours. After the completion of the reaction, the reaction solution was purified by extraction with water/ethyl acetate and then the separated ethyl acetate solution was dried over sodium sulfate and concentrated under reduced pressure to obtain 15.0 g of a compound (A)-1 represented by formula (3) shown below:

[Chemical formula 26]

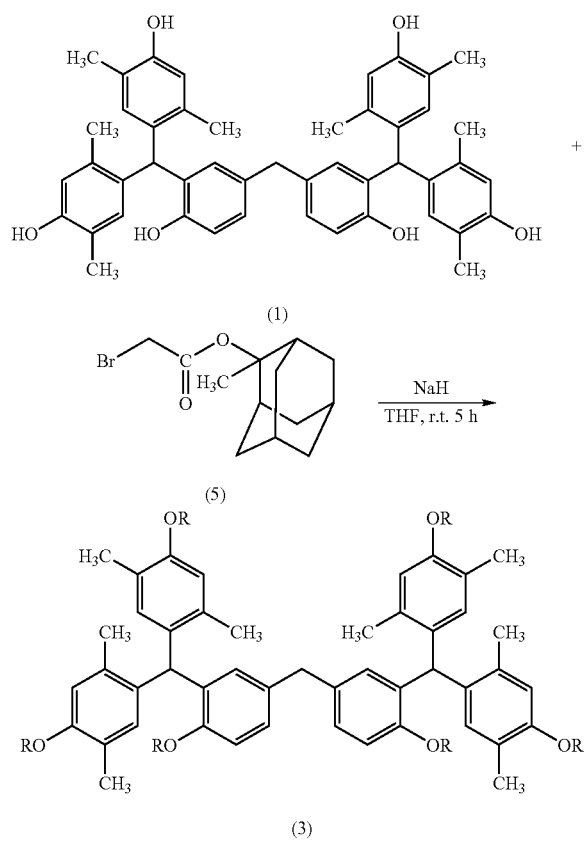

[wherein, in the formula (3), R represents a hydrogen atom or a group represented by formula (5') shown below].

[Chemical formula 27]

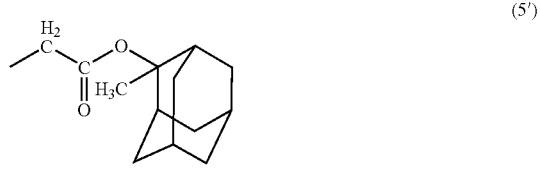

The compound (A)-1 was analyzed by $^1$H-NMR. The results are shown below. The results revealed that the protection ratio per molecule of the compound (A)-1 (the proportion (mol %) in which R is a group represented by formula (5') shown below among R in formula (3) shown above) is 30.2 mol %.

$^1$H-NMR (deuterated dimethyl sulfoxide (DMSO), internal standard: tetramethylsilane) δ=8.75-9.08(m, 3.76H), 6.33-6.80(m, 14H), 5.60-5.96(m, 2H), 4.48-4.75(m, 3.62H), 3.41-3.63(m, 2H), 1.35-2.25 (m, 58.43H).

Determination of the compound (A)-1 was conducted by reverse phase liquid chromatography under the following conditions and the ratio of the n protector protected with n (n=0 to 6) phenolic hydroxyl groups existing in the polyphenol compound (1) was determined from the proportion of the peak area. Assuming that the compound (A)-1 is composed of 1,000 molecules, the existing number of each protector was calculated. The results are shown in Table 1. As shown in Table 1, the compound (A)-1 contained from a 0 protector to a 4 protector.

<Conditions of Reverse Phase Liquid Chromatography>
Apparatus: SERIES1100 manufactured by Hewlett-Packard Company
Column: MG type manufactured by Shiseido Co., Ltd. (functional group: Particle size of C18: 3 μm, Inner diameter of column: 4.6 mm, Length of column: 75 mm)
Detection wavelength: 280 nm
Flow rate: 2.0 mL/min
Measuring temperature: 45° C.
Measuring time: 0 to 22 min
Amount of sample injected: 1.0 μL
Sample concentration (solid content): about 1.3% by weight (diluted with THF)
Eluant
  0 to 1 min: (1) Pure water/THF=60/40 (weight ratio)
  1 to 21 min: gradually changed from (1) to the following composition (2)
  21 to 22 min: (2) Pure water/THF=10/90 (weight ratio)

TABLE 1

| (A)-1 | 0 protector | 1 protector | 2 protector | 3 protector | 4 protector |
|---|---|---|---|---|---|
| Number of protective groups n | 0 | 1 | 2 | 3 | 4 |
| Protection ratio (%) | 0 | 16.7 | 33.3 | 50 | 66.7 |
| Existing number (per 1,000 molecules) | 114 | 309 | 354 | 186 | 37 |

Next, the compound (A)-1 was purified by silica gel column chromatography under the following conditions to obtain a compound (A)-2.

Purification conditions by silica gel column chromatography: Silica gel (Wakol Gel C100) was used and ethyl acetate was used as the eluent. Also, silica gel was used in an amount 20 times by weight larger than that of the substrate (compound (A)-1). The column tube used had a diameter of 9 cm.

After filling the column with a sample obtained by dissolving 10 g of the compound (A)-1 in a small amount of chloroform, the eluent was poured into the column and the resulting effluent was referred to as a fraction A. The fraction A was dried over sodium sulfate and then concentrated under reduced pressure to obtain a compound (A)-2.

Next, the compound (A)-2 was conducted a second purification by silica gel column chromatography under the following conditions in the same manner above to obtain a compound (A)-3 of 2.5 g.

Second purification conditions by silica gel column chromatography: Silica gel (Wakol Gel C200) was used and chloroform: MEK=9:1 was used as the eluent. Also, silica gel was used in an amount 20 times by weight larger than that of the substrate (compound (A)-2). The column tube used had a diameter of 9 cm.

Determination of the compound (A)-3 was conducted by reverse phase liquid chromatography in the same manner, and the number of protective groups, the protection ratio and the existing number in the compound (A)-3 was determined. The results are shown in Table 2. As shown in Table 2, the compound (A)-3 contained only 2 protector.

TABLE 2

| (A)-3 | 0 protector | 1 protector | 2 protector | 3 protector | 4 protector |
|---|---|---|---|---|---|
| Number of protective groups n | 0 | 1 | 2 | 3 | 4 |
| Protection ratio (%) | 0 | 16.7 | 33.3 | 50 | 66.7 |
| Existing number (per 1,000 molecules) | 0 | 0 | 1000 | 0 | 0 |

Next, the compound (A)-3 has proved to be a mixture of two kinds of structural isomers, the compounds (A)-4 and (A)-5 below ((A)-4:(A)-5=2:1 at a proton-NMR ratio) measured by the proton-NMR.

Then, each structural isomers was separated by column chromatography under the following conditions and structures thereof were identified.

Purification conditions by column chromatography: Silica gel (Wakol Gel C200) was used and ethyl acetate:hexane=3:1 was used as the eluent. Also, silica gel was used in an amount 20 times by mass larger than that of the substrate (compound (A)-3). The column tube used had a diameter of 9 cm.

Operation: the compound (A)-4 of 1.5 g and the compound (A)-5 of 0.5 g were obtained in the same manner as the operation above.

$^1$H-NMR data of the compound (A)-4 (heavy DMSO, internal standard: tetramethylsilane): δ(ppm)=9.01 s 2H(—OH (1)), 8.80 s 2H(—OH (4)), 6.28-6.80 m 14H, 5.70 s 2H(—CH (6)), 4.69 s 4H(—CH$_2$ (9)), 3.46 s 2H(—CH$_2$ (11)), 1.25-2.21 m 58H.

[Chemical formula 28]

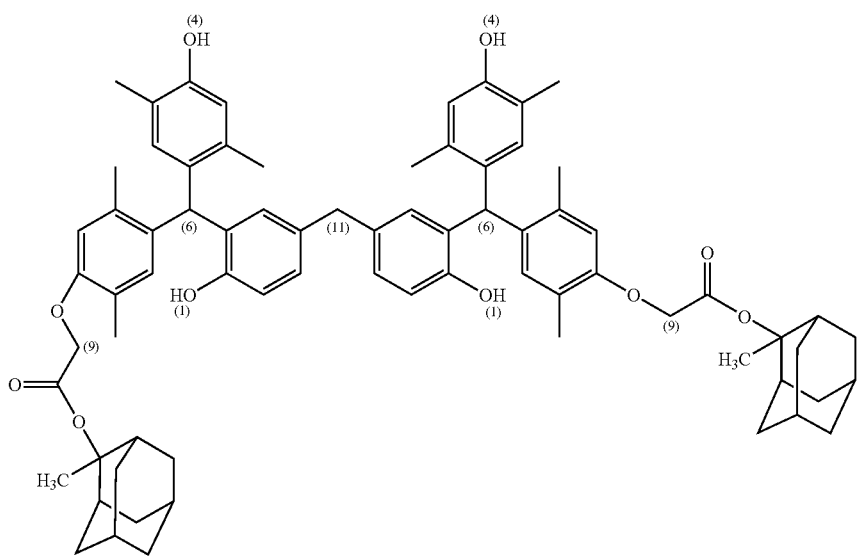

(A)-4

$^1$H-NMR data of the compound (A)-5 (heavy DMSO, internal standard: tetramethylsilane): δ(ppm)=8.90 s 1H(—OH (2)), 8.98 s 1H(—OH (3)), 8.83 s 2H(—OH (5)), 6.28-6.80 m 14H, 5.67 s 1H(—CH (7)), 5.64 s 1H(—CH (8)), 4.68 s 4H(—CH$_2$ (10)), 3.52 s 2H(—CH$_2$ (12)), 1.25-2.21 m 58H.

[Chemical formula 29]

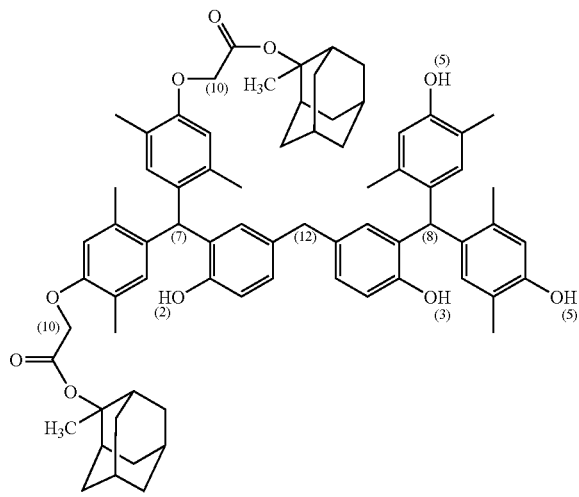

(A)-5

Examples 1 to 3 and Comparative Example 1

The compounds (A)-1, (A)-3 to (A)-5 obtained in Preparation Examples were mixed with the respective components shown in Table 3 below, and then dissolved to obtain positive resist composition solutions.

In Table 3, the numerical values within parentheses mean the amount (parts by weight). Also, the abbreviations in Table 4 mean as follows.

(B)-1: Triphenylsulfoniumnonafluoro-n-butanesulfonate (D)-1: Tri-n-octylamine (E)-1: Salicylic acid (S)-1: PGMEA Then, each of the resulting positive resist composition solutions was uniformly applied on an 8 inch silicon substrate using a spinner, and a PAB treatment was then conducted under baking (PAB) conditions of 110° C. for 90 seconds, thus forming a resist film (thickness: 150 nm).

The resist film was subjected to writing (exposure) using an electron-beam direct writing system (HL-800D (VSB) (manufactured by Hitachi, Ltd.), acceleration voltage (70 kV)), and a PEB treatment was then conducted under baking (PEB) conditions of 100° C. for 90 seconds. Subsequently, development was conducted for 200 seconds using an aqueous 2.38 weight % solution (23° C.) of tetramethylamnonium hydroxide (TMAH), followed by rinsing with pure water for 30 seconds. As a result, a 120 nm line-and-space (L/S) 1:1 pattern was formed.

The resulting resist pattern was observed from the top using a scanning electron microscope manufactured by Hitachi, Ltd. (Measuring SEM, S-9220) and LER was evaluated according to the following criteria. The results are shown in Table 3.
A: small line undulation
B: large line undulation

TABLE 3

| | Component (A) | Component (B) | Component (D) | Component (E) | Component (S) | LER |
|---|---|---|---|---|---|---|
| Example 1 | (A)-3 [100] | (B)-1 [12.6] | (D)-1 [0.38] | (E)-1 [0.15] | (S)-1 [1150] | A |
| Example 2 | (A)-4 [100] | (B)-1 [12.6] | (D)-1 [0.38] | (E)-1 [0.15] | (S)-1 [1150] | A |
| Example 3 | (A)-5 [100] | (B)-1 [12.6] | (D)-1 [0.38] | (E)-1 [0.15] | (S)-1 [1150] | A |
| Comparative Example 1 | (A)-1 [100] | (B)-1 [12.6] | (D)-1 [0.38] | (E)-1 [0.15] | (S)-1 [1150] | B |

As is apparent from the above results, resist patterns obtained using the positive resist compositions of Examples 1 to 3 exhibited less line undulation and reduced LER.

In contrast, a resist pattern obtained using the positive resist composition of Comparative Example 1 exhibited large line undulation and inferior LER.

Industrial Applicability

The compound of the present invention is capable of forming a resist pattern with a reduced level of roughness and ideal for use within the positive resist composition and the resist pattern forming method, and the positive resist composition.

The invention claimed is:

1. A composition comprising a plurality of compounds represented by a general formula (I) below:

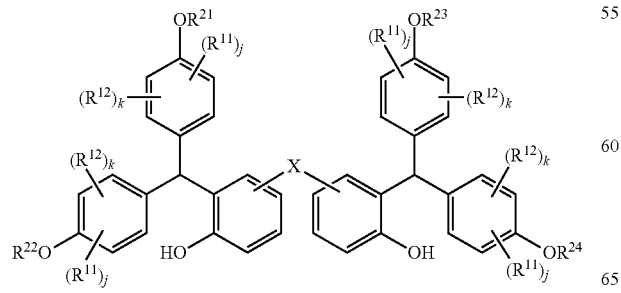

[wherein, in formula (I), $R^{11}$ and $R^{12}$ each represents, independently, an alkyl group of 1 to 10 carbon atoms or an aromatic hydrocarbon group, and may include a hetero atom in the structure;
$R^{21}$ to $R^{24}$ each represents, independently, a hydrogen atom or an acid dissociable, dissolution inhibiting group, and two of the group of $R^{21}$ to $R^{24}$ represent a hydrogen atom and the others represents an acid dissociable, dissolution inhibiting group; j and k each represents, independently, an integer of 0 or 1 or more, and j +k is 4 or less; X is a group represented by general formulas (Ia) or (Ib) below],

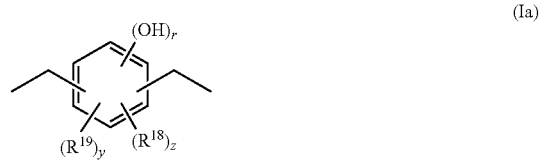

-continued

[wherein, in formula (Ia), $R^{18}$ and $R^{19}$ each represents, independently, an alkyl group of 1 to 10 carbon atoms or an aromatic hydrocarbon group, and may include a hetero atom in the structure;
and r, y, and z each represents, independently, an integer of 0 or 1 or more, and r+y+z represents 4 or less], wherein there is substantially no variation in the number of the acid dissociable, dissolution inhibiting groups within molecules of the composition.

2. The composition according to claim 1, wherein the acid dissociable, dissolution inhibiting group is at least one member selected from the group consisting of an alkoxycarbonylalkyl group represented by the general formula (p1) below and an alkoxyalkyl group represented by the general formula (p2) below

-continued (p2)
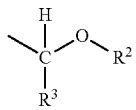

[wherein, $R^1$ and $R^2$ each represents, independently, a straight-chained, branched-chained, or cyclic alkyl group, and may include a hetero atom in the structure thereof; $R^3$ represents a hydrogen atom or a lower alkyl group; and n' represents an integer from 1 to 3]

3. The composition represented by the general formula (II) below according to either claim 1 or 2, wherein (II)
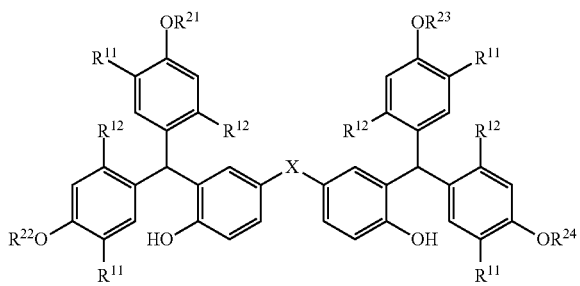

[wherein, in formula (II), $R^{11}$ and $R^{12}$ each represents, independently, an alkyl group of 1 to 10 carbon atoms or an aromatic hydrocarbon group, and may include a hetero atom in the structure thereof; $R^{21}$ to $R^{24}$ each represents, independently, a hydrogen atom or an acid dissociable, dissolution inhibiting group, and two of the group of $R^{21}$ to $R^{24}$ represents a hydrogen atom and the others represents an acid dissociable, dissolution inhibiting group; X is a group represented by general formulas (Ia) or (Ib) below], (Ia)
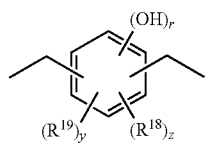

(Ib)
$\overset{H_2}{\underset{\diagdown}{C}}$

[wherein, in formula (Ia), $R^{18}$ and $R^{19}$ each represents, independently, an alkyl group of 1 to 10 carbon atoms or an aromatic hydrocarbon group, and may include a hetero atom in the structure;
and r, y, and z each represents, independently, an integer of 0 or 1 or more, and r+y+z represents 4 or less], wherein
there is substantially no variation in the number of the acid dissociable, dissolution inhibiting groups within molecules of the composition.

4. A positive resist composition comprising a base material component (A) which exhibits increased alkali solubility under an action of an acid, and an acid generator component (B) which generates an acid upon exposure, wherein
the base material component (A) is a compound (A1) represented by the general formula (I) below:

(I)

[Formula I image]

[wherein, in formula (I), $R^{11}$ and $R^{12}$ each represents, independently, an alkyl group of 1 to 10 carbon atoms or an aromatic hydrocarbon group, and may include a hetero atom in the structure thereof; $R^{21}$ to $R^{24}$ each represents, independently, a hydrogen atom or an acid dissociable, dissolution inhibiting group, and two of the group of $R^{21}$ to $R^{24}$ represents a hydrogen atom and the others represents an acid dissociable, dissolution inhibiting group; j and k each represents, independently, an integer of 0 or 1 or more, and j +k is 4 or less; X is a group represented by general formulas (Ia) or (Ib) below], (Ia)

[Formula Ia image]

(Ib)
$\overset{H_2}{\underset{\diagdown}{C}}$

[wherein, in formula (Ia), $R^{18}$ and $R^{19}$ each represents, independently, an alkyl group of 1 to 10 carbon atoms or an aromatic hydrocarbon group, and may include a hetero atom in the structure; and r, y, and z each represents, independently, an integer of 0 or 1 or more, and r+y+z represents 4 or less], wherein
there is substantially no variation in the number of the acid dissociable, dissolution inhibiting groups within molecules of the composition.

5. The positive resist composition according to claim 4, wherein the acid dissociable, dissolution inhibiting group of the compound (A1) is at least one an acid dissociable, dissolution inhibiting group selected from the group consisting of an alkoxycarbonylalkyl group represented by the general formula (p1) below and an alkoxyalkyl group represented by the general formula (p2) below.

(p1)
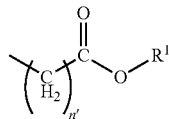

-continued

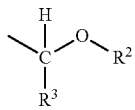
(p2)

[wherein, $R^1$ and $R^2$ each represents, independently, a straight-chained, branched-chained, or cyclic alkyl group, and may include a hetero atom in the structure; $R^3$ represents a hydrogen atom or a lower alkyl group; and n' represents an integer from 1 to 3]

6. The positive resist composition of claim 4, wherein the compound (A1) is a compound (A1-1) represented by the general formula (II) below:

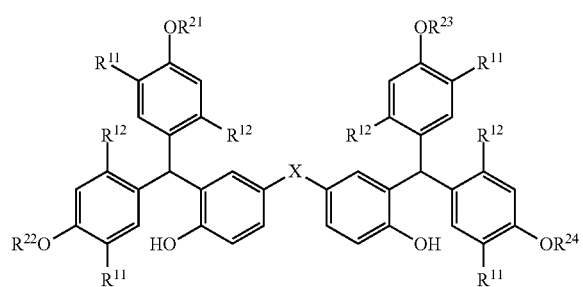
(II)

[wherein, in formula (II), $R^{11}$ and $R^{12}$ each represents, independently, an alkyl group of 1 to 10 carbon atoms or an aromatic hydrocarbon group, and may include a hetero atom in the structure thereof; $R^{21}$ to $R^{24}$ each represents, independently, a hydrogen atom or an acid dissociable, dissolution inhibiting group, and two of the group of $R^{21}$ to $R^{24}$ represents a hydrogen atom and the others represents an acid dissociable, dissolution inhibiting group; X is a group represented by general formulas (Ia) or (Ib) below]

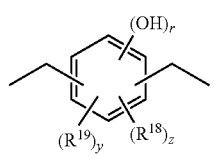
(Ia)

(Ib)

[wherein, in formula (Ia), $R^{18}$ and $R^{19}$ each represents, independently, an alkyl group of 1 to 10 carbon atoms or an aromatic hydrocarbon group, and may include a hetero atom in the structure;

and r, y, and z each represents, independently, an integer of 0 or 1 or more, and r+y+z represents 4 or less], wherein there is substantially no variation in the number of the acid dissociable, dissolution inhibiting groups within molecules of the composition.

7. The positive resist composition according to any one of claims 4 to 6, further comprising a nitrogen-containing organic compound (D).

8. A resist pattern forming method comprising:
forming a resist film on a substrate using the positive resist composition according to any one of claims 4 to 6,
conducting exposure of the resist film, and
developing the resist film to form the resist pattern.

* * * * *

UNITED STATES PATENT AND TRADEMARK OFFICE
CERTIFICATE OF CORRECTION

PATENT NO. : 8,389,197 B2
APPLICATION NO. : 11/994602
DATED : March 5, 2013
INVENTOR(S) : Takako Hirosaki et al.

It is certified that error appears in the above-identified patent and that said Letters Patent is hereby corrected as shown below:

In the Specification

At Column 1, Line 4, Below "Forming Method" insert --RELATED APPLICATIONS This application is the U.S. National Phase filing under 35 U.S.C. §371 of PCT/JP2006/313103, filed Jun. 30, 2006, which designated the United States and was published in a language other than English, which claims priority under 35 U.S.C. §119(a)-(d) to Japanese Patent Application No. 2005-196132 filed Jul. 5, 2005. The content of these applications is incorporated herein by reference in their entireties.--.

At Column 1, Lines 11-12, Below "method." delete "Priority is claimed on Japanese Patent Application No. 2005-196132, filed Jul. 5, 2005, the content of which is incorporated herein by reference.".

At Column 5, Line 51, Change "above," to --above.--.

At Column 6, Line 65, Change "3]" to --3].--.

At Column 13, Line 50-51, Change "molecules" to --molecules,--.

At Column 21, Line 46 (Approx.), Change "(B3-3)," to --(B-3),--.

Signed and Sealed this
Fifteenth Day of October, 2013

Teresa Stanek Rea
*Deputy Director of the United States Patent and Trademark Office*

CERTIFICATE OF CORRECTION (continued)
U.S. Pat. No. 8,389,197 B2

At Column 22, Line 39 (Approx.), Change "α-(n-butylsulfonyloxyimino)-11-cyclopentenylacetonitrile," to --α-(n-butylsulfonyloxyimino)-1-cyclopentenylacetonitrile,--.

At Column 28, Line 33 (Approx.), Change "hereafter" to --(hereafter--.

At column 35, Line 11, Change "tetramethylamnonium" to --tetramethylammonium--.

In the Claims

At Column 37, Line 12, In Claim 2, Change "3]" to --3].--.

At Column 37, Line 53, In Claim 3, Change "$R^{18}$and" to --$R^{18}$ and--.

At Column 38, Line 58, In Claim 5, Change "below." to --below--.

At Column 39, Line 13 (Approx.), In Claim 5, Change "3]" to --3].--.